United States Patent [19]

Leiboff

[11] Patent Number: 4,637,814
[45] Date of Patent: Jan. 20, 1987

[54] METHOD AND APPARATUS FOR INTESTINAL IRRIGATION

[76] Inventor: Arnold Leiboff, 20 Wendell St., Hempstead, N.Y. 11550

[21] Appl. No.: 720,571

[22] Filed: Apr. 5, 1985

[51] Int. Cl.$^4$ ............................................. A61M 1/00
[52] U.S. Cl. ...................................... 604/27; 604/28; 604/39; 604/41
[58] Field of Search ...................... 604/27, 28, 39–45, 604/54, 96, 275, 276, 278, 279

[56] References Cited

U.S. PATENT DOCUMENTS

| | | | |
|---|---|---|---|
| 1,596,847 | 8/1926 | Mallory | 604/40 |
| 2,148,541 | 2/1939 | Dierker | 604/40 |
| 3,508,546 | 4/1970 | Rogers et al. | 604/30 |
| 4,117,847 | 10/1978 | Clayton | 604/96 |
| 4,190,059 | 2/1980 | Holt | 604/27 |

Primary Examiner—C. Fred Rosenbaum
Assistant Examiner—J. L. Kruter
Attorney, Agent, or Firm—Steinberg & Raskin

[57] ABSTRACT

Method and apparatus for unidirectional irrigation of at least a portion of the gastrointestinal tract between a point of access thereto and a distant or remote point of the tract. The distal end of an irrigating tube is passed through a point of access to the gastrointestinal tract to a distant point in the tract beyond which irrigation is not desired. The irrigating tube has one or more apertures formed therein only in the region substantially proximate to the distal end thereof. In the case where the portion of the tract being irrigated is not already occluded at the distant point, the tract is then occluded at that point whereupon irrigant is introduced into the irrigating tube through a proximal end thereof whereby the irrigant passes through the irrigating tube and is discharged therefrom through the aperture into the gastrointestinal tract at the region of the occluded distant point thereof and flows unidirectionally through the tract towards and out from the point of access. The apparatus includes a large diameter drain tube positioned at the point of access in communication with the portion of the gastrointestinal tract being irrigated and an irrigating tube having an irrigating lumen in which the irrigant aperture is formed. When positioned, the irrigating tube passes through the drain tube and has a length such that its distal end in which the irrigant aperture is formed is situated substantially at the occluded distant point of the tract with its proximal end adapted to be fluidly connected to a source of irrigant. The drain tube incorporates an effluent discharge conduit which has a relatively large diameter to enhance the flow rate of effluent from the tract portion being irrigated.

21 Claims, 39 Drawing Figures

METHOD AND APPARATUS FOR INTESTINAL IRRIGATION

BACKGROUND OF THE INVENTION

The present invention relates to methods and apparatus for irrigating the gastrointestinal tract or portions thereof.

The importance of a clean colon to the success of colonic surgery has been well established. This type of surgery is still plagued with septic complications, most of which arise from endogenous intestinal bacteria that contaminate the operative field during the surgical procedure. Surgeons have learned that they can significantly reduce the chances that a patient will develop a wound infection, intraabdominal sepsis, or an anastomotic dehiscense, following surgery if the colon has been effectively cleansed before the bowel wall is violated.

Some controversy exists as to the best method of bowel preparation for patients who undergo surgery of the colon. Many regimens of mechanical and antimicrobial preparations have been developed to reduce the concentration of colonic bacteria below critical levels.

The most widely used method of preparing the bowel for surgery comprises dietary restrictions to clear fluids, laxatives, enemas and one of multiple antibiotic combinations administered orally on the day prior to surgery. Many devices have been designed for the efficient administration of enemas. All such devices force fluid through the bowel in a retrograde direction in a repeating sequence and rely on peristalsis to flush out the irrigant and colonic waste. Such bidirectional flow renders the process slow and inefficient due to the fact that contaminants are washed back and forth within the bowel. The degree to which the bowel can be cleaned by such prior devices is therefore severely limited.

The conventional technique for bowel preparation as described above has many disadvantages. It achieves suboptimal cleansing and must be restricted to elective cases. Administration is highly variable and is distressing to the patient. It prolongs hospital confinement and causes nutritional deprivation. It promotes the development of antibiotic resistant intestinal flora and has adverse metabolic effects. The antibiotics employed can be toxic. Preparation of the patient requires a significant labor investment by hospital staff and can be wasteful and even harmful should surgery be cancelled or postponed. Furthermore, preparing a patient for colonic surgery in the conventional manner entails considerable expense.

In order to avoid some of the disadvantages of conventional bowel cleansing techniques as described above, an alternative method has been recently developed, sometimes referred to as "whole bowel irrigation." According to this technique, on the day prior to surgery a large volume of irrigating fluid is administered to the patient either by mouth or by way of a nasogastric tube, at a rate which exceeds the capacity of the gut to absorb the irrigant. The unabsorbed fluid washes the colon as increased peristaltic activity flushes it through and out the rectum. Although this technique may shorten hospitalization, it also suffers from certain serious disadvantages. In particular, cleansing is still suboptimal. Fluid overload and electrolyte imbalance may be produced and the procedure is therefore contraindicated in those patients having cardiac, renal, or hepatic problems. This technique is also distressing to patients, causing nausea and vomiting on occasion, and also requires substantial labor investment by the hospital. Variations of this procedure, such as catharsis induced by ingestion of oral mannitol, have been attempted but suffer similar or other disadvantages.

Despite the variety of preoperative bowel cleansing techniques in use, none give uniformly good results. A large percentage of patients prepared for elective colonic surgery are found at laparotomy to have a fair degree of fecal loading. Those patients operated on emergently invariably have unclean bowel. To deal with a bowel loaded with feces encountered at surgery several methods of intraoperative bowel preparation have been devised.

Instillation of antimicrobial agents into the bowel lumen prior to enterotomy has been suggested. See, for example "Intestinal Antisepsis" by Edgar J. Poth, M.D., American Journal of Surgery, Vol. 88, Nov., 1954; "Experimental Evaluation of 'Instant' Preparation of the Colon with Povidone-Iodine" by Frank E. Jones, M.D., Jerome J. DeCosse, M.D., and Robert E. Condone, M.D., Surgical Clinics of North America, Vol. 55, No. 6, Dec., 1975; and "Bacteriologic and Systemic Effects of Intraoperative Segmental Bowel Preparation with Povidone Iodine," by Arango et. al., Archives of Surgery, Vol. 114, Feb., 1979. However, these methods fail to remove the fecal matter, which cannot be completely sterilized. When the bowel is incised or opened virulent material can still escape, infect the parietes, and soil and obscure the anastomotic field.

Intraoperative irrigating techniques have also been suggested. See for example "Safety in Colonic Resection," by Edward G. Muir, Proceedings of the Royal Society of Medicine, Vol. 61, Apr. 1968; and "Intraoperative Irrigation of the Colon to Permit Primary Anastomosis," by H. A. Dudley, A. G. Radcliffe, and D. McGeehan, British Journal of Surgery, Vol. 67, 1980. These techniques, however, are clumsy, may easily result in spillage of bowel contents and peritoneal contamination, leave significant amounts of fecal material in the bowel, and do not affect the concentration of bacteria within the remaining feces. Some intraoperative irrigating techniques (see, e.g., "Colonic Decompression and Lavage in Anterior Resection of the Rectosigmoid," by H. Clay Alexander, Surgery, Obstetrics, and Gynecology, Vol. 135, 1972; and "Intraoperative Chaffin Sump Recto-Colonic Irrigation" by G. Bruce Thow, M.D., Diseases of the Colon and Rectum, Vol. 19, No. 4, May–June, 1976) amount to little more than intraoperative enemas.

Others have suggested combining both irrigation and antimicrobials. However, such techniques are clumsy and cannot accomodate high volumes of irrigant at high rates of flow. (See, e.g., "Impromptu Bowel Cleansing and Sterilization," by Marvin L. Gliedman et. al., Surgery, Vol. 43, No. 2, Feb., 1958).

Whenever unidirectional antegrade irrigation has been employed, an enterotomy for placement of a proximal irrigating catheter was performed, exposing the operative field to a risk of contamination even before cleansing was begun.

Thus, an improved method for intraoperative bowel preparation which can cleanse the colon so safely, effectively, and quickly, that it could be recommended for routine use in elective cases as well as in emergency laparotomies, would be of great value.

SUMMARY OF THE INVENTION

Accordingly, it is an object of the present invention to provide new and improved methods and apparatus for irrigating the gastrointestinal tract whereby morbidity, such as postoperative abdominal sepsis and wound infection, as well as mortality of colonic procedures, are reduced by producing a cleaner and more sterile bowel.

Another object of the present invention is to provide new and improved methods and apparatus for intestinal irrigation which overcome the aforementioned disadvantages of conventional preoperative and intraoperative bowel preparation techniques.

Still another object of the present invention is to provide new and improved methods and apparatus for intraoperative irrigation of the colon.

A further object of the present invention is to provide new and improved methods and apparatus for unidirectional, either retrograde or antegrade, irrigation of the colon with such high volumes and rates of flow that bowel cleansing can be performed in both elective and emergency cases in a quick and thorough yet safe manner at the time of laparotomy.

Another object of the present invention is to provide new and improved methods and apparatus for intraoperative unidirectional irrigation of the colon that rely on transit of fluid through the bowel in response to pressure gradients rather than peristaltic activity.

Still another object of the present invention is to provide new and improved methods and apparatus for intraoperative irrigation of the colon in an exclusively antegrade direction without cutting, piercing, or violating the bowel wall in any manner, thus precluding transmural contamination of the operative field as a result of the irrigation procedure.

A further object of the present invention is to provide new and improved methods and apparatus for intraoperative irrigation of the colon which permits a single stage procedure rather than multiple procedures with temporary colostomy to be performed by achieving adequate intraoperative preparation of the colon thereby avoiding morbidity and mortality associated with multiple procedures and closures of colostomies.

Another object of the present invention is to provide new and improved methods and apparatus for intraoperative irrigation of the intestines and cleansing the bowel which are safer than conventional arrangements and which do not produce the physiological, nutritional and metabolic disturbances that preoperative bowel preparation techniques can cause.

Still another object of the present invention is to provide new and improved methods and apparatus for intraoperative irrigation of the colon and intestines wherein the bowel can be efficiently cleansed above a stenosis or obstruction.

A further object of the present invention is to provide new and improved methods and apparatus for intraoperative irrigation of the intestines wherein the bowel can be efficiently cleansed above and below a stenosis or partial obstruction simultaneously using a single instrument.

A still further object of the present invention is to provide new and improved methods and apparatus for intraoperative irrigation of the intestines which will not promote the proliferation of antibiotic resistant bacteria as do the techniques employing oral antibiotics.

Another object of the present invention is to provide new and improved methods and apparatus for intraoperative irrigation of the colon wherein air can be evacuated from the bowel prior to irrigation, the distended bowel can be quickly decompressed during irrigation, and the bowel can be completely emptied at the conclusion of irrigation.

Still another object of the present invention is to provide new and improved apparatus for intraoperative irrigation of the colon including a large diameter drain tube that can be inserted either through the anus or through an enterotomy whereby resistance to outflow of effluent is minimized.

A further object of the present invention is to provide new and improved apparatus for intraoperative irrigation of the colon including a large diameter drain tube that can be easily inserted through the anus or through an enterotomy with an obturator and which is soft enough to minimize the possibility of damage to the bowel wall.

A still further object of the present invention is to provide new and improved apparatus for intraoperative irrigation of the bowel and which provides a closed system which prevents contamination of the operating room, either by microorganisms or by odor.

A still further object of the present invention is to provide new and improved methods and apparatus for intraoperative irrigation of the colon for cleansing the bowel that permits a patient undergoing an elective colonic procedure to maintain his regular diet and activity until the day prior to surgery, that reduces the length of preoperative hospital confinement for many elective procedures on the large bowel and which inflicts substantially little discomfort on the patient in contrast to other preoperative mechanical cleansing techniques.

Another object of the present invention is to provide new and improved methods and apparatus for intraoperative irrigation of the bowel whereby suction can be applied through the entire portion of the bowel being cleansed.

Still another object of the present invention is to provide new and improved methods and apparatus for intraoperative irrigation of the bowel wherein the temperature of the irrigant can be monitored rapidly and regulated to be at, above or below body temperature.

A further object of the present invention is to provide new and improved apparatus for intraoperative irrigation of the bowel including a mobile unit for storage and pumping of irrigant, and collection of bowel effluent, that is inexpensive, compact, and lightweight, and which can be readily transferred between operating rooms.

A still further object of the present invention is to provide new and improved methods and apparatus for intraoperative irrigation of the bowel which, in addition to performing a cleansing function, can also be used to cool or warm the body in an efficient manner.

Yet another object of the present invention is to provide new and improved apparatus for intraoperative irrigation of the bowel which is inexpensive in manufacture and easy to use.

A still further object of the present invention is to provide new and improved apparatus for intraoperative irrigation of the bowel including drain and irrigating tubes which are so inexpensive in manufacture as to be disposable after use thereby obviating the cost of cleaning.

Briefly, in accordance with the present invention, these and other objects are attained by providing a method and apparatus for continuous unidirectional irrigation of at least a portion of the gastrointestinal tract between an occluded distant or remote point of the tract and a point of access to the tract which may comprise the anus, a transected end of the bowel or an enterotomy in the bowel. The apparatus includes a large diameter drain tube, including an effluent discharge conduit, which is positioned during use at the point of access in communication with the point of the gastrointestinal tract being irrigated and an irrigating tube having aperture means including one or more irrigating apertures formed therein only in the region substantially proximate to the distal end thereof. In use the irrigating tube passes through the drain tube and has a length such that its distal end in which the irrigant aperture is formed is situated substantially at the occluded distant point of the tract with its proximal end adapted to be fluidly connected to a source of irrigant. Irrigant is pumped through the irrigating tube and is discharged therefrom through the aperture means into the region of bowel lumen proximate to the occluded distant point thereof. The irrigant will flow unidirectionally through the gastrointestinal tract portion towards the drain tube positioned in the point of access whereupon the effluent constituted by the bowel contents entrained in the irrigant enters into the drain tube and is discharged through the effluent discharge conduit. The exclusive unidirectional flow in the gastrointestinal tract eliminates the sequential backwash of contamination which renders enema techniques inefficient.

Waste material is washed out of the bowel through the drain tube which has a large internal diameter. By providing a large cross-sectional area, minimal resistance to outflow is achieved and irrigant can be moved through the bowel by pressure gradient rather than peristaltic activity. Continuous undirectional irrigation and low outflow resistance together permit higher rates of irrigation and faster and more thorough cleansing of the bowel than can be achieved by any other method previously devised.

Various embodiments of the drain tube and the irrigating tube are disclosed. A combination of a specific drain tube and a specific irrigating tube is chosen to irrigate a particular patient based upon the specific anatomy and pathology of the patient's bowel, as defined by preoperative testing or operative findings.

The embodiments of the drain tube meant to be inserted per anum into the rectum each have a large diameter primary tubular section, an expandable retention cuff, a cuff inflation-deflation lumen and a side arm constituting the effluent discharge conduit to which a lightweight flexible hose is connected to communicate with one or more collection containers. Additionally, certain embodiments of the drain tube have a second, smaller diameter side arm which connects with a suction lumen of a double lumen embodiment of irrigating tube described below.

One embodiment of the irrigating tube has a single lumen construction through which irrigant is infused into the bowel. This embodiment of irrigating tube is best applied in small children or infants whose small size makes a separate suction lumen (described below) impractical or unnecessary, or in adults when there is a complete obstruction in the distal colon and the surgeon desires to clean only the short segment of bowel distal to the lesion. Since the single lumen irrigating tube is provided with apertures only near its distal end, it can function without leakage when only its tip is inserted, such as in the case of administration of an enema.

Should suction be desired, the proximal end of the tube can always be detached from the tubing conduit from the pump and attached to an extension from effluent collection chambers.

Another embodiment of the irrigating tube has a double lumen construction, one of the lumens being for irrigation and the other of the lumens being for the application of suction to the bowel. The suction lumen has apertures over long segments of the distal portions of the irrigating tubes. The smaller side arm of a double side armed drain tube connects with the suction lumen of the double lumen irrigating tube, transmits suction to the suction lumen and channels drainage from the suction lumen into the drain tube. By effectively transmitting suction throughout the entire colon, bowel evacuation is enhanced. The suction lumen also serves to empty the bowel of air prior to and during irrigation. This prevents the creation of air pockets which can prevent the irrigant from washing the underlying bowel wall. The suction lumen also efficiently empties the bowel of irrigant at the completion of irrigation. Thus, it is useful to present a completely empty bowel to the surgeon in order to facilitate manipulation of the viscera, to improve visibility within the abdominal cavity, and prevent spillage of any fluid that still might contain viable microorganism. The suction lumen also permits efficient irrigation of the bowel proximal to a stenosing lesion or functional obstruction produced by bowel contraction around the colonic tube. Once a double lumen irrigating tube is passed beyond a stenosis, the suction lumen insures minimal cross-sectional area for outflow of irrigant. Suction applied to the lumen helps draw effluent out of the obstructed region, and the suction level may be increased if required.

Another embodiment of irrigating tube, in addition to including the suction lumen, has an irrigating lumen through which apertures are formed along a relatively long segment of the distal portion of the tube. These apertures, which are small in comparison to the apertures in the suction lumen, are preferably spaced farther apart as one moves proximally along the tube and/or may be progressively smaller in diameter. This arrangement enables uniform irrigation along the entire distal portion of the tube and is used where there is a stenotic lesion. Having irrigation apertures in the section of the tube distal to a stenosis allows simultaneous dilitation in cleansing of the bowel both proximal and distal to the stenosis. Should apertures not be provided in the segment distal to the stenosis, most of the irrigant suctioned through the stenosis would remain within the suction lumen and the distal bowel would remain collapsed and not be cleansed.

The apparatus in accordance with the invention further includes means for storing, pumping and collecting the irrigant and intestinal waste material. According to the illustrated embodiment, a mobile unit is provided which includes storage reservoirs with spigots and temperature gauges, an immersion heater to enable regulation of irrigant temperature, a variable speed peristaltic pump regulated by both a potentiometer on the pump housing and a foot switch potentiometer, and collection containers which connect to a suction regulator with an overflow safety trap. Vacuum is suppled to the unit from a centrally piped vacuum system. A conduit formed of flexible elastomeric tubing communicates with all of the storage reservoirs, passes through the pump head, and has a pair of arms, one of which communicates with the irrigating lumen of the irrigating tube and the other of which is shunted to a pressure relief valve. The pressure relief valve is connected on its outflow side to a flow indicator which in turn is connected through shunt tubing to a collection container. The pressure relief valve is adjusted so that when there is an obstruction to flow within the pump tubing conduit or colonic tube, such for example, as a kink in the tubing, or if the tubing is mistakenly clamped, the valve will open and shunt fluid into the collection containers before any tubing connection fails due to the increased pressure. A flow indicator in the line notifies the operator that irrigant is being shunted and that there is therefore something obstructing flow. A lightweight flexible large diameter hose communicates with the drain tube and a large bore valve on the mobile unit, which connects to the suction containers.

In accordance with one embodiment of a method of the invention for cleaning the bowel using the apparatus described above and wherein the anus constitutes the point of access to the tract portion being cleansed, an obturator is fitted through the primary tubular section of the drain tube, which may in this case be termed a rectal tube. The rectal tube is then inserted into the patient's rectum through the anus prior to surgical draping. The obturator is then removed, the proximal end of the primary tubular section is capped or plugged, and the retention cuff is inflated. One end of a lightweight flexible hose is connected to the larger side arm of the rectal tube and its other end is connected to a collection container via the large bore valve. The patient is then draped and laparotomy is performed.

If the bowel is found to contain a large amount of formed feces and it is anticipated that there will be difficulty advancing an irrigation tube through the feces, bowel cleansing is begun by administering an intraoperative enema using the instruments described above. The tubing conduit from the pump may be connected to the smaller side arm of the rectal tube in the case where a double side arm tube is being used, or to the irrigating lumen of the irrigating tube. If the latter technique is employed, the cap or plug on the primary tubular section of the rectal tube is removed and the tip of the irrigating tube is inserted. The tapered cuff member of the colonic tube is then slid forward around the tubular member and plugged into the rectal tube. The large bore outflow valve is then closed. Alternatively, a clamp is placed on the lightweight flexible outflow hose. By depressing the foot switch, the surgeon can then infuse irrigant into the bowel and by massaging the bowel the solid feces can be softened and liquified. This can be expedited by adding a detergent compound, such as docusate sodium, to the irrigant. Once the feces is liquified, the large bore outflow valve may be opened, suction may be applied to the outflow system, and much of the liquid stool can be evacuated.

The irrigating tube can then be easily and quickly passed through the bowel until its distal tip reaches the occluded distant point of the bowel portion being irrigated, e.g., an obstructing lesion, or the terminal ileum or cecum. To facilitate passage of the irrigating tube, an assistant pushes from below and the surgeon guides the tube by manipulating the bowel.

The proximal end of the irrigating lumen is then connected to the tubing conduit from the pump, and if a double lumen irrigating tube is used, the proximal end of the suction lumen is connected to the smaller side arm of the rectal tube. The proper level of suction is set and the potentiometer on the pump housing is adjusted for the desired range of pump speeds. The surgeon then places a non-crushing intestinal occluding clamp on the bowel just proximal to the tip of the irrigating tube and is thus ready to begin irrigation.

By depressing the foot switch potentiometer the surgeon infuses irrigant into, and gently massages, the bowel. In the adult patient, about 20 liters of irrigant is used. When the surgeon desires, an assistant may close the spigot of the reservoir containing the primary irrigant, generally water or saline, with or without a detergent, and may open the spigot of a reservoir containing a secondary irrigant, usually an antiseptic or carcinolytic agent. When the irrigation is completed and the colon has been suction dried, the irrigating tube is withdrawn. In this manner an exclusively unidirectional and in this case antegrade irrigation of the bowel lumen is accomplished.

In addition to speed and efficacy, the method of the invention can be performed more safely than any other method of intraoperative irrigation since no incisions of any kind are made in the bowel wall prior to cleansing the lumen. Therefore, the possibilities that insecure ligations or other errors in technique may lead to contamination of the operative field are eliminated. Irrigant can be delivered at high rates through the small lumen of the irrigating tube by the peristaltic pump which, by virtue of the fact that the irrigant never touches the pump mechanism, cannot itself contaminate the irrigant. The surgeon, by depressing the foot switch potentiometer, controls the speed of the pump and therefore the rate of irrigation and consequent distension of the bowel. This, and the fact that a segment of bowel distended by irrigant can be immediately decompressed throughout its entire length by application of suction to the suction lumen of the irrigating tube, ensures against overdistension of the bowel and adds another dimension of safety to the procedure.

The fact that the bowel can be cleansed quickly, safely and thoroughly renders the invention ideal for use in routine elective cases as well as emergency procedures. The invention is applicable even in cases of partial bowel obstruction utilizing a stiff, thin, double lumen irrigating tube which can be pushed through a partial obstruction. Moreover, the invention can be effectively used even in the case where a high grade or complete obstruction exists. Thus, where the bowel obstruction is significant or complete, the same apparatus described herein, or modifications thereof, can be used to cleanse the bowel through a colotomy or through the end of a transected bowel, rather than through the anus. In such cases, the irrigation of the bowel tract portion will still occur unidirectionally, either in an antegrade or retrograde direction.

BRIEF DESCRIPTION OF THE DRAWINGS

A more complete appreciation of the present invention and many of the attendant advantages thereof will be readily understood by reference to the following detailed description when considered in connection with the accompanying drawings in which.

DESCRIPTION OF THE PREFERRED EMBODIMENTS

Figure 1:
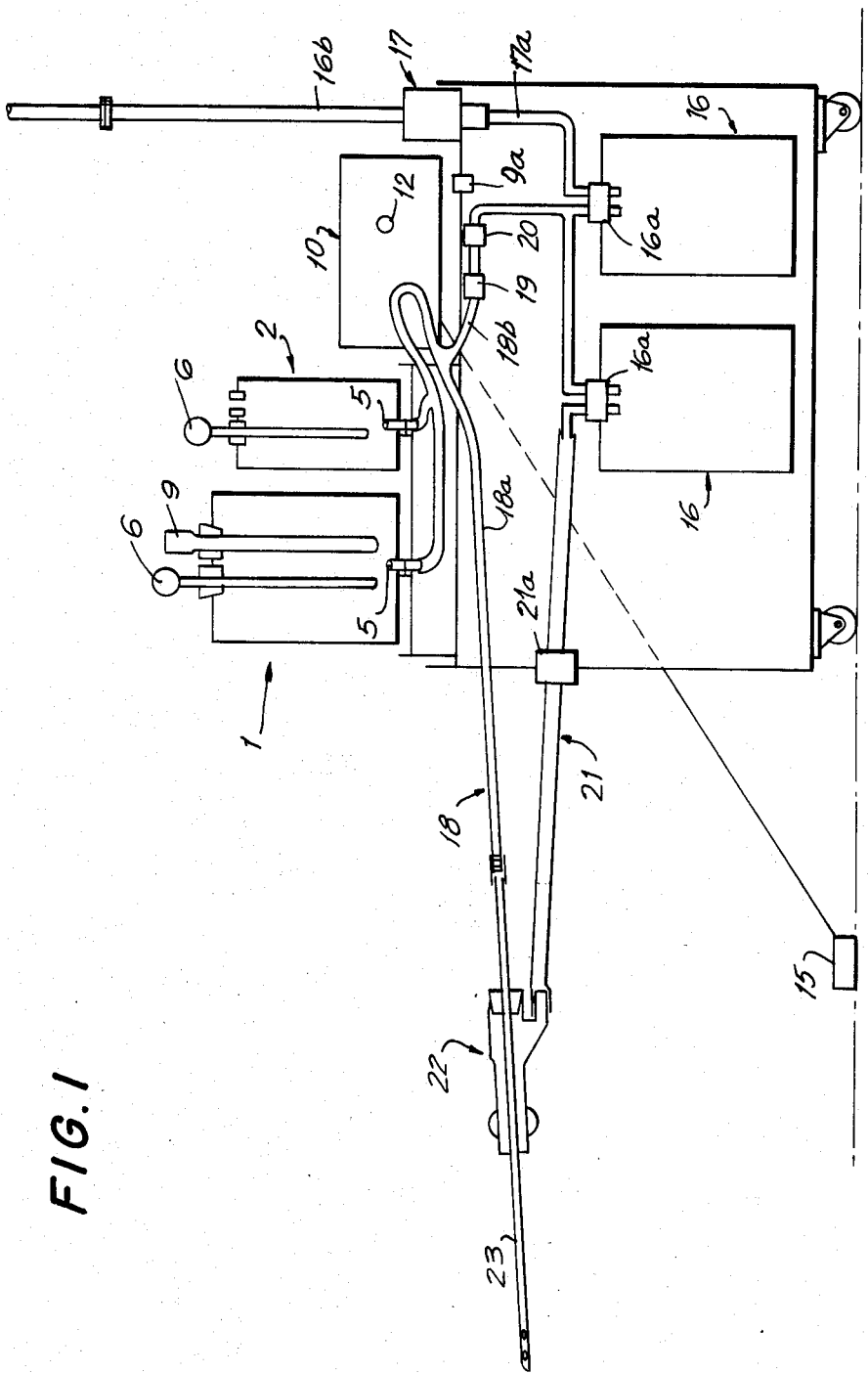
FIG. 1 is a schematic view of one embodiment of irrigation apparatus in accordance with the present invention including a single side arm drain tube and single lumen irrigating tube.

Referring now to the drawings wherein like reference characters designate identical or corresponding parts throughout the several views, and more particularly to FIG. 1, irrigation apparatus in accordance with the present invention includes a source of primary irrigant in the form of a large primary irrigant reservoir 1, a source of secondary irrigant in the form of a smaller, secondary irrigant reservoir 2, means for transferring irrigant from the reservoirs to the irrigating tube in the form of a variable speed peristaltic pump 10, means for receiving relatively large volumes of bowel effluent in the form of collection containers 16, a drain tube 22, an irrigating tube 23, and tubing means 18 and 21 for carrying irrigant from the reservoirs 1 and 2 to the irrigating tube 23 and for carrying effluent from the drain tube 22 to the collection containers 16.

Primary irrigant, such for example, as water, saline or other known solution, is stored in the large reservoir 1. A compound with detergent properties, such as docusate sodium, may be added to the irrigant in order to speed dissolution of hard feces and to help cleanse the mucosal surface of adherent feces, microorganisms, and the tenacious mucous in which microorganisms inbed.

The smaller reservoir 2 contains a secondary irrigant, generally an antiseptic. After irrigation with the primary irrigant the bowel is washed with antiseptic in order to kill any residual microorganisms. Solutions such as Clorpactin WS90 or Povidone-Iodine may be used for this purpose. Both reservoirs 1 and 2 are preferably constructed of a lightweight transparent plastic, such as polycarbonate, with calibrations inscribed on the front side for visual observation. Spigots 5 provided in the base of each of the reservoirs 1 and 2 are used to select either the primary or secondary irrigant.

An immersion heater 9, controlled by a switch 9a, and temperature guages 6 are provided so that the temperature of the irrigants can be precisely regulated. The irrigants are normally infused at body temperature to protect against excessive cooling of the patient or thermal injury to the bowel. The heater 9 is of sufficient wattage to be capable of heating the contained irrigant to body temperature in a matter of minutes.

The variable speed peristaltic pump 10 is a conventional appliance and functions to transfer irrigant from the reservoirs 1 and 2 to the irrigating tube 23. The peristaltic mechanism of the pump operates on the tubing 18 with no direct contact of the pump with the irrigant and, therefore, eliminates the danger of contamination of the irrigant and bowel with microorganisms or substances which may accumulate on the pump head. A potentiometer 12 is adjusted to set the maximum pump speed while a foot switch potentiometer 15 regulates the pump speed between zero and the maximum speed selected by the potentiometer 12. The pump 10 is preferably designed so that tubing 18 of several different diameters can be interchangably used.

The collection containers 16 are hermetically sealed by means of appropriate tube fittings 16a. A suction line 16b connected to a central vacuum source (not shown) communicates with the interiors of containers 16. A suction regulator 17 provided with an overflow safety trap 17a controls the suction level within the collection chamber 16.

Tubing means 18 comprises tubing formed preferably of flexible elastomeric material. The tubing 18 has a proximal end which is bifurcated into a pair of arms which are connected to the spigots 5 of reservoirs 1 and 2. The tubing 18 passes through the pump head and is again bifurcated into an irrigant inflow tube portion 18a and a shunt portion 18b in which a pressure relief valve 19 is connected. The outflow tube portion 18a is connected to the proximal end of irrigating tube 23. Pressure relief valve 19 is adapted to open and shunt irrigant through shunt tube portion 18b into the collection chamber 16 when the pressure within the tubing 18 approaches the pressure at which the tubing connections will fail, such as when an obstruction exists to irrigant flow within the system. A flow indicator 20 is installed between the pressure relief valve 19 and collection containers 16 which provides an indication to the surgeon that fluid is being shunted to containers 16 and that there is possibly an obstruction to flow in the system.

Tubing means 21 comprises tubing formed of lightweight, flexible material and functions to channel effluent from the rectal tube 22 to the collection containers 16. It is important that tubing 21 be constructed such that it will not collapse when suction is applied during operation. A valve 21a is installed between tubing 21 and the collection container 16 to interrupt outflow so that the bowel may be filled when the apparatus is used to administer enemas through the drain tube 22.

The drain tube 22 is preferably constructed in accordance with one of two main embodiments while the irrigating tube 23 is preferably constructed in accordance with one of three main embodiments.

Figure 2:
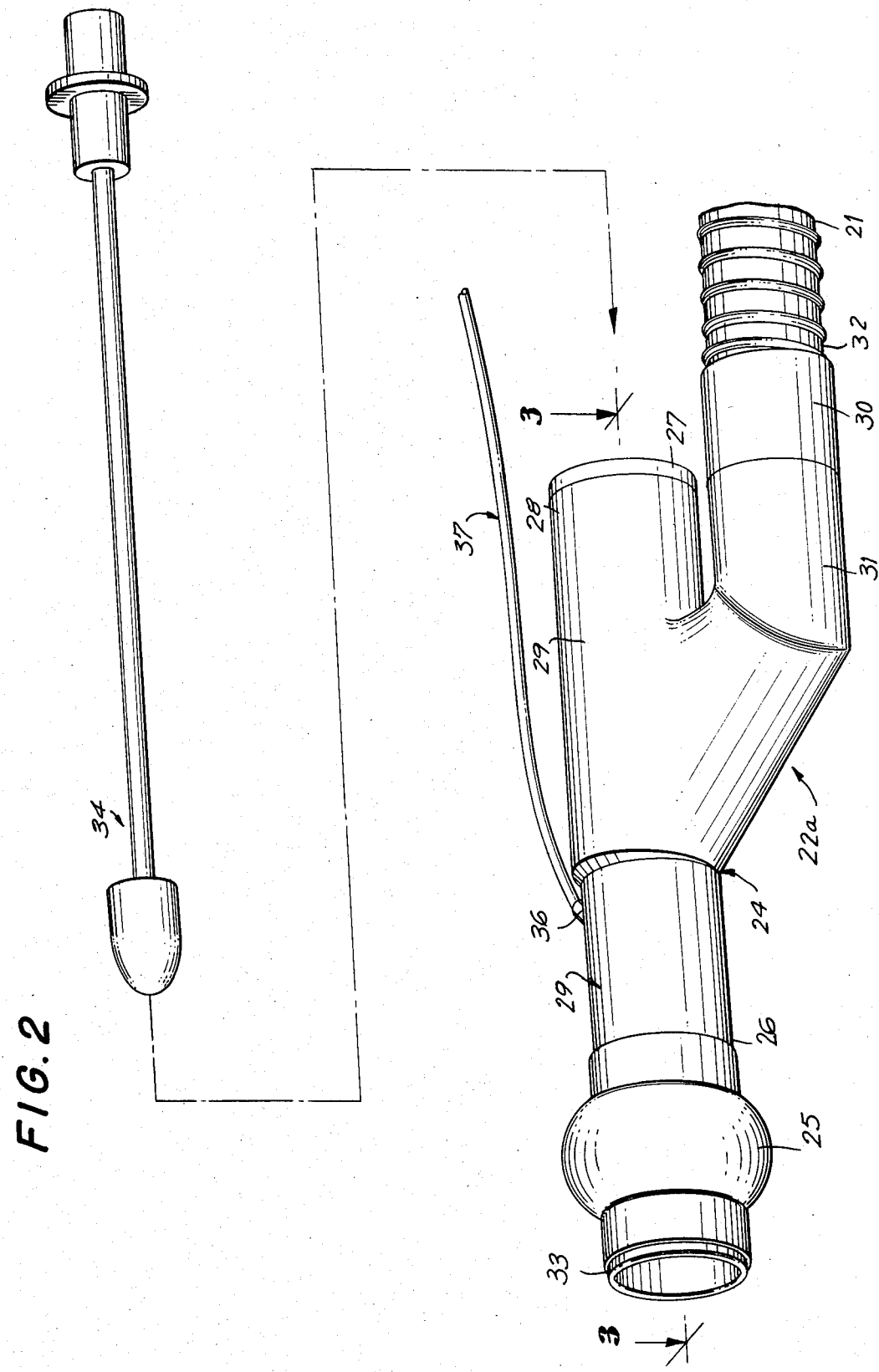
FIG. 2 is a perspective view of a first modification of a first embodiment of a drain tube in accordance with the invention, namely, a single side arm drain tube, shown with an obturator for use in the insertion of the drain tube.
Figure 3:
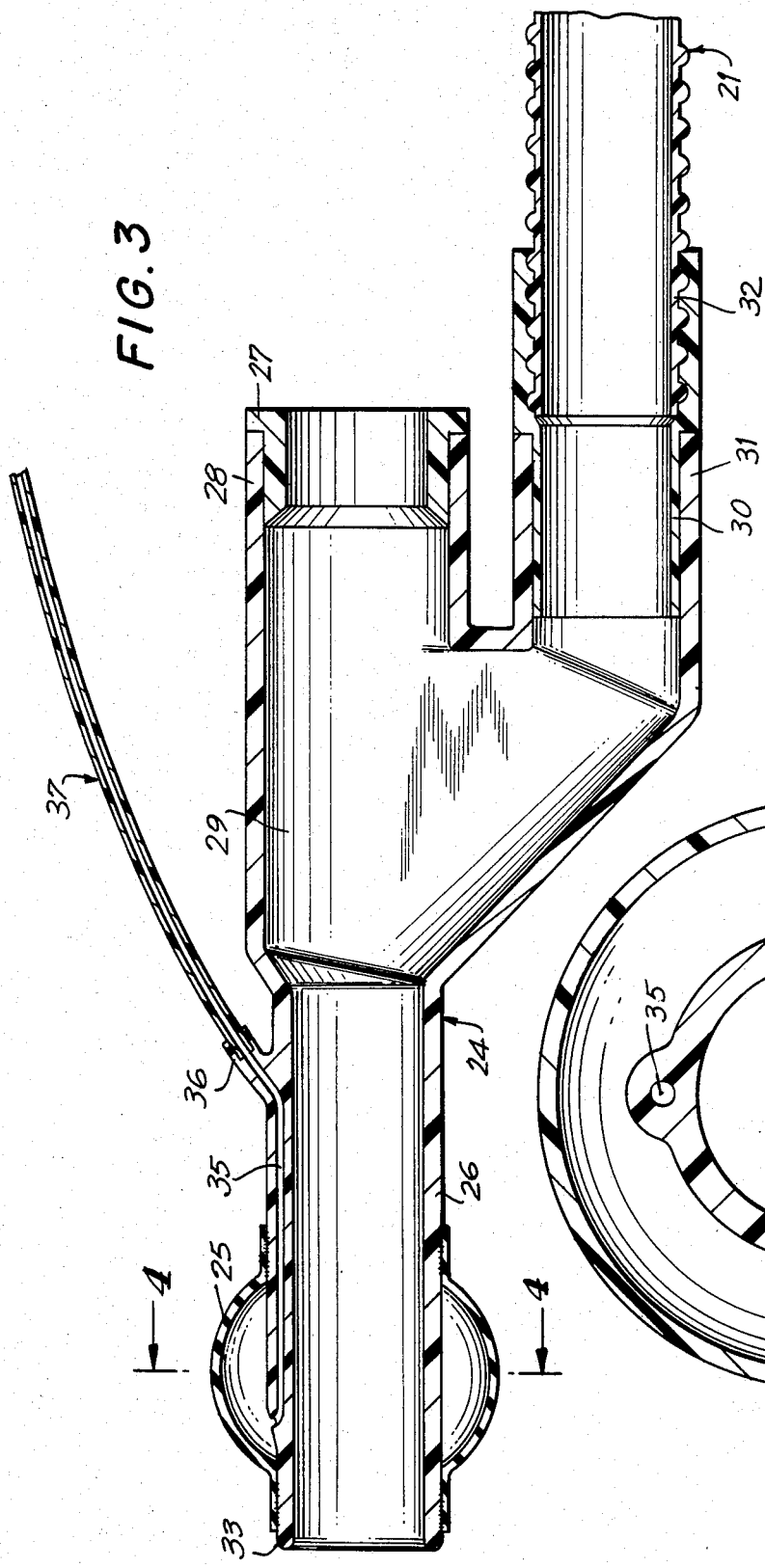
FIG. 3 is a longitudinal section view of the single side arm drain tube taken along line 3—3 of FIG. 2.
Figure 4:
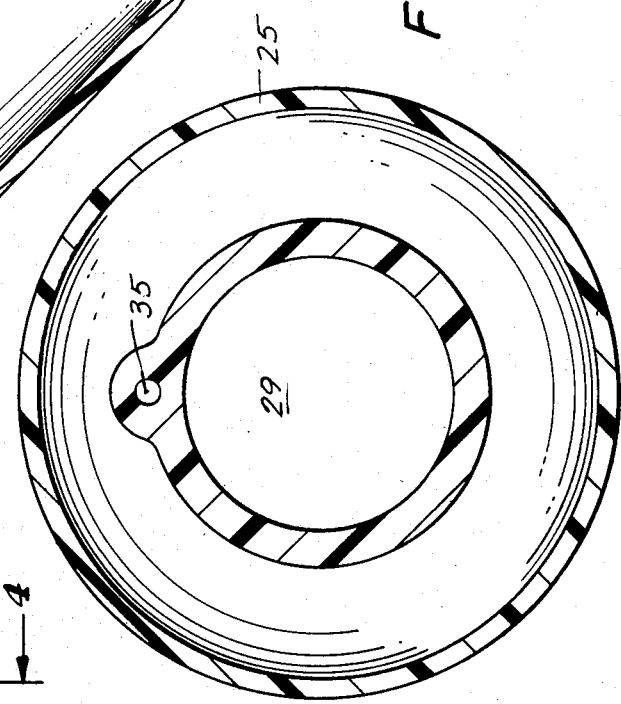
FIG. 4 is a transverse cross-sectional view of the single side arm drain tube taken along line 4—4 of FIG. 3, the expandable retention cuff shown in its inflated condition.

Referring to FIGS. 2-4 wherein a first modification of a first embodiment of a drain tube, designated 22a, is illustrated, the drain tube 22a comprises a smooth surfaced body 24 formed of a flexible, preferably transparent elastomer, an expandable retention cuff 25 provided at the distal portion 26 of tube body 24, a bushing 27 formed of rigid polymer fitted into the proximal end 28 of the primary tubular section 29 of body 24 and an end fitting 30 fitted into the proximal end of the side arm 31. The end 32 of outflow hose 21 is adapted to be connected to the side arm 31 through the end fitting 30.

The distal end 33 of drain tube 22a is formed with rounded edges for atraumatic insertion of the tube into the point of access to the tract portion being cleansed, such as the anus, with the aid of an obturator 34 (FIG. 2). The distal end 33 may have other conventional shapes such, for example, as a tapered bulbous shape, as long as its minimum internal diameter is not significantly less than the smallest diameter of the primary tubular section 29. Obturator devices may be designed especially for use with the drain tube, e.g., including structure to secure the obturator in place in the drain tube.

An internal cuff inflation-deflation lumen 35 (FIG. 3) fluidly communicates the expandable retention cuff 25 and a proximal cuff lumen opening 36 provided in the central region of the body 24 of drain tube 22a. A segment of tubing 37 may be attached to the cuff lumen opening at one of its ends and to an inflation device at its other end.

Although the retention cuff is shown as being mounted near the distal end of the drain tube, it may alternatively be mounted more proximally in which case side openings may be formed in the drain tube distal to the retention cuff in order to drain stool that accumulates around the drain tube tip during irrigation. Moreover, the expandable cuff 25 may be mounted as illustrated in FIG. 3 or, alternatively, may be provided with an invaginated reentrant section at the distal end of the cuff in which case the largest diameter of the inflated cuff will approach closer to the distal end of the drain tube leaving less space around the distal tip for feces to accumulate.

The bushing 27 adapted to be inserted into the proximal end 28 of the primary tubular section 29 of drain tube 22a is separately formed from a rigid polymer or the like and is fixed to the drain tube by a solvent-sealing or other conventional method. The rigid bushing 27 functions to provide an unyielding seat for the pliable tapered cuff member 38 (e.g., FIG. 10) of the irrigating tube 23. Thus, as described in greater detail below, when the tapered cuff member 38 is inserted into bushing 27 with some force, the inner bore 39 (FIG. 11) of the tapered cuff member is compressed around the outer diameter of the tubular member of the irrigating tube to form a seal which prevents leakage of effluent at that junction during irrigation.

The end fitting 30 which is fixed within the proximal end of the large diameter side arm 31 is preferably formed of a flexible vinyl elastomer or the like with internal threads being formed on the portion which extends beyond the end of the drain tube side arm 31. The threads engage the corrugated outer diameter of the end 32 of the outflow hose 21. Alternatively, threads may be molded into the end of the side arm 31 itself in which case the end fitting 30 may be eliminated.

Any one of a number of conventional lightweight flexible tube materials may be used for outflow hose 21. Preferably, tubing 21 has a smooth bore in order to reduce the chances of clogging. Alternatively, a simple flexible tube 40 (FIG. 5) made of polyvinylchloride and having a sufficient diameter may be used in lieu of the outflow hose 21.

Figure 5:
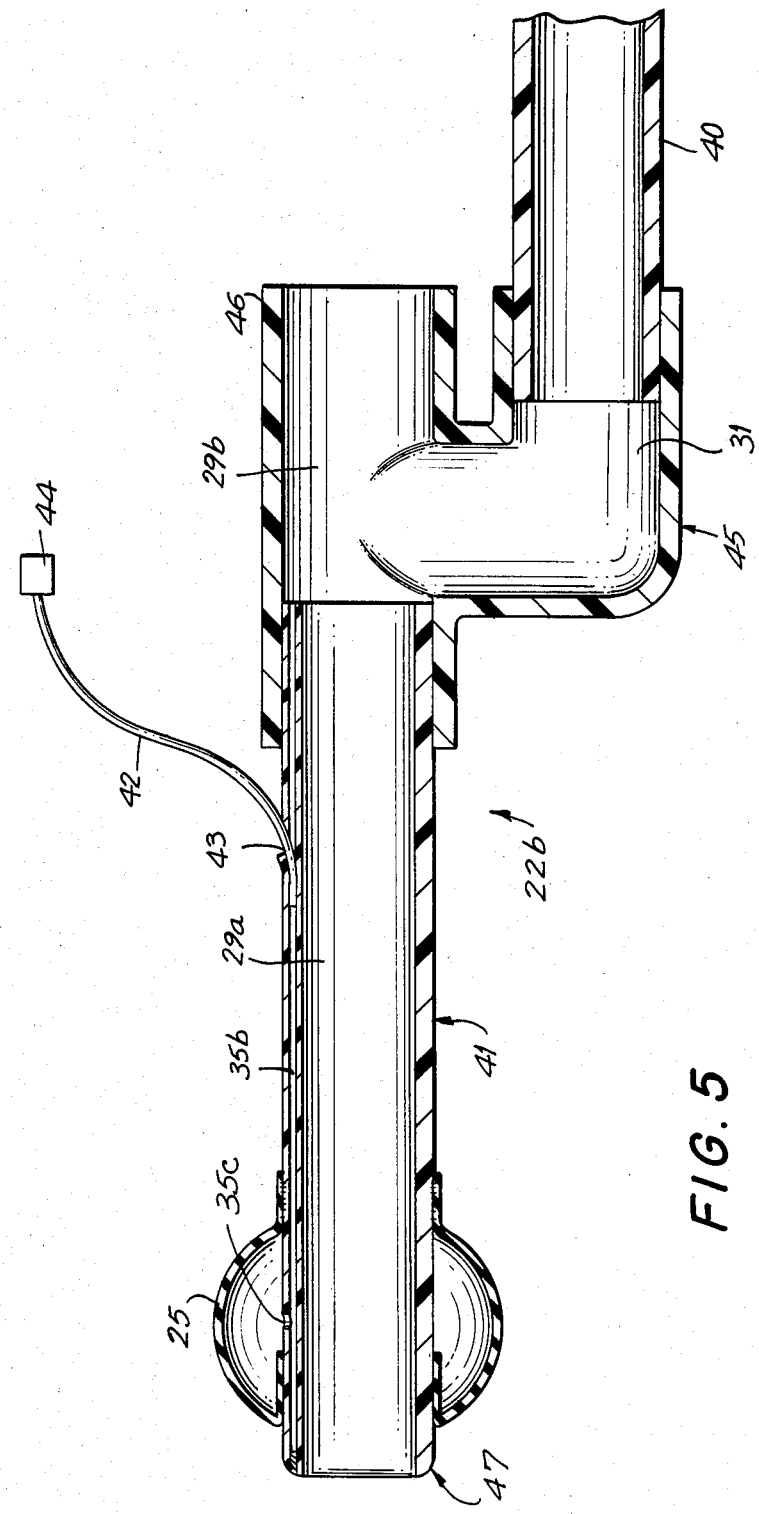
FIG. 5 is a longitudinal section view of a second modification of the first, i.e., single side arm, embodiment of a drain tube in accordance with the invention.

Referring to FIG. 5, a second modification 22b of a single side arm drain tube is illustrated. According to this modification of the first embodiment, the distal portion of the body of the drain tube 22b encompassing the distal portion 29a of the primary tubular section and the expandable cuff inflation-deflation lumen comprises a tubular body 41 formed by an extruding process rather than by a molding process as in the case of the embodiment illustrated in FIGS. 2–4. A tubular extension 42 is fixed at its distal end to a side opening 43 of the inflation-deflation lumen by solvent sealing and is attached to a valve or other inflation device 44 on its proximal end. The proximal end of the extruded body 41 is attached to the distal end of a molded proximal end portion 45 which may be formed of a flexible or rigid polymer or the like. If formed of a rigid polymer, the addition of a rigid bushing, such as bushing 27, to the proximal end of the primary tubular section 29 is not required. Thus, the molded proximal end portion 45 defines the proximal end 29b of the primary tubular section as well as a side arm 31 into which outflow tube 40 is inserted. The proximal end 29b of the primary tubular section, defined by molded end portion 45, may be in any configuration so as to obtain a matching configuration to the tapered cuff members of the irrigating tubes. The distal end 47 of the drain tube 22b can be rounded by heating and molding or by any other method so as to ensure atraumatic insertion. A retention cuff 25 is mounted on the distal portion of the drain tube and communicates with the inflation deflation lumen 35b through aperture 35c.

Figure 6:
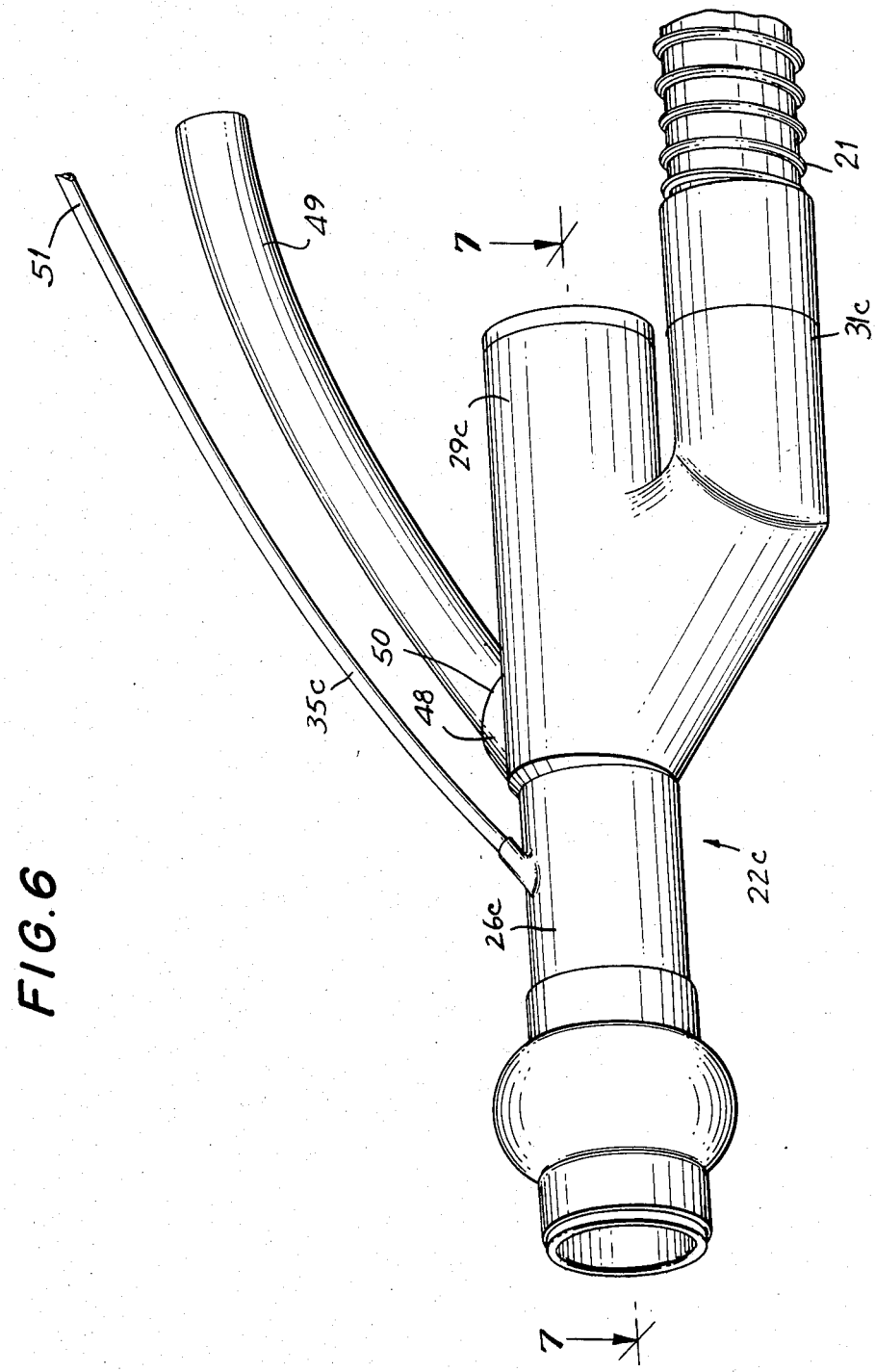
FIG. 6 is a perspective view of a first modification of a second embodiment of a drain tube in accordance with the invention, namely, a double side arm drain tube.
Figure 7:
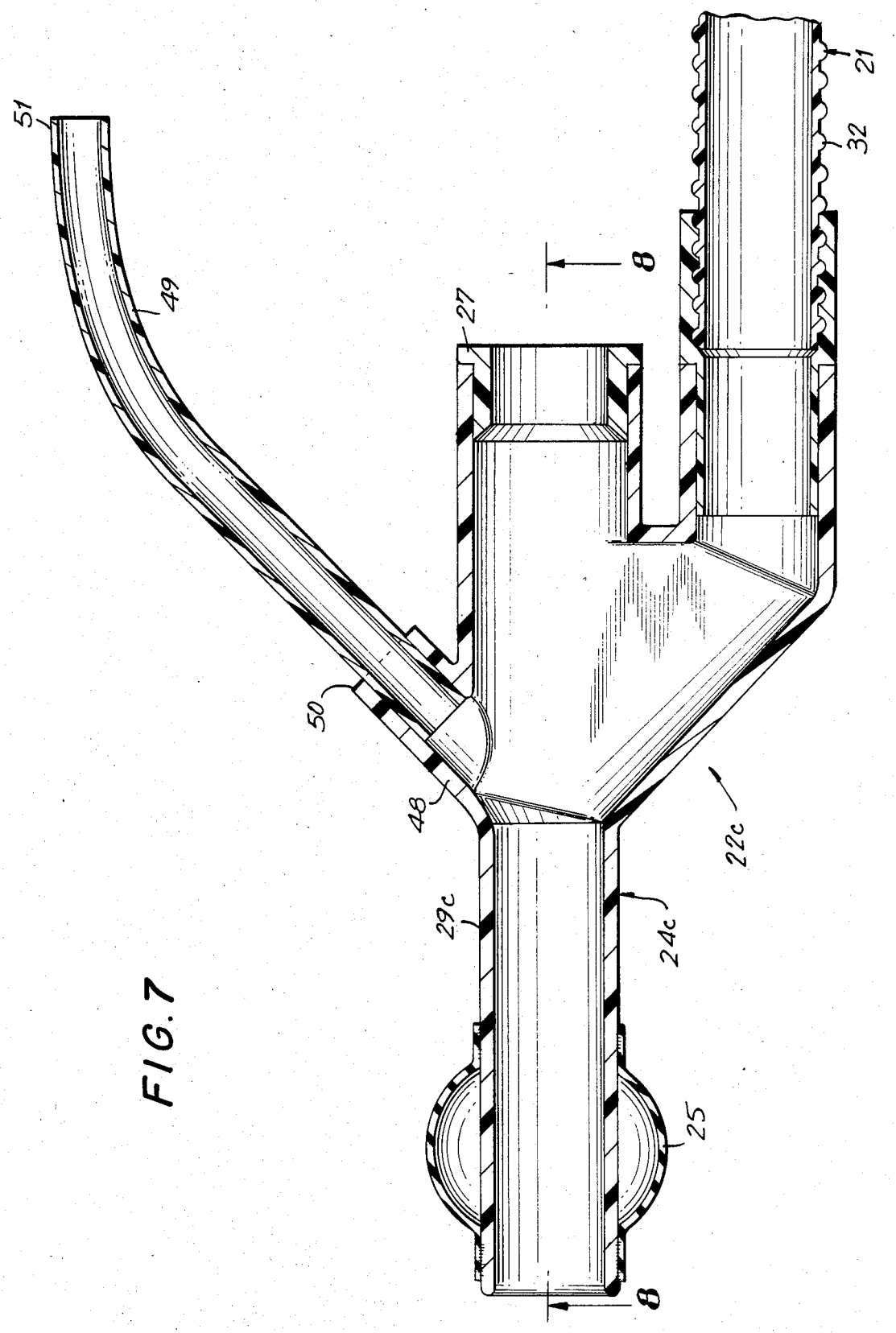
FIG. 7 is a longitudinal section view taken along line 7—7 of FIG. 6.
Figure 8:
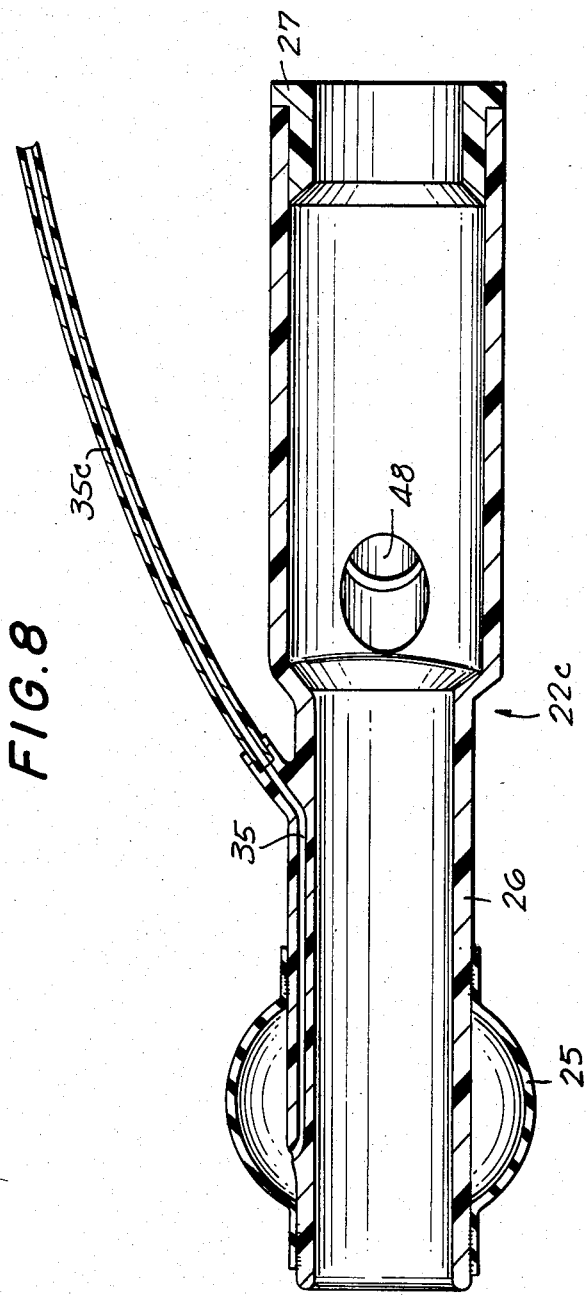
FIG. 8 is a longitudinal section view taken along line 8—8 of FIG. 6.

A first modification of a second embodiment of a drain tube, namely, a double side arm drain tube, is illustrated in FIGS. 6–8 and designated 22c. Drain tube 22c is substantially similar to the single side arm embodiment illustrated in FIGS. 2–4 with the exception that a second, reduced diameter side arm 48 is provided.

Figure 9:
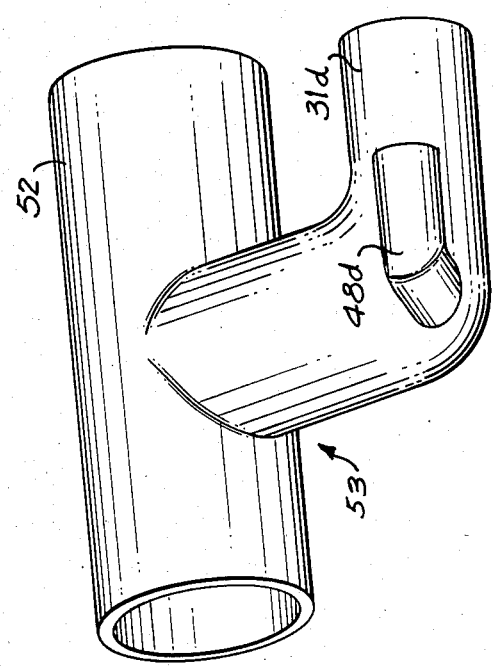
FIG. 9 is a perspective view of a molded proximal portion forming a component of a second modification of the second, i.e. the double side arm, embodiment of a drain tube in accordance with the invention.

The second side arm 48 may extend directly outwardly from the primary tubular section 29c as shown or, alternatively, the second side arm 48 may extend from the first, larger diameter side arm 31c, such as shown in FIG. 9. The second side arm 48 may even be part of the outflow hose 21 instead of the drain tube 22.

One end of a segment of extruded flexible elastomeric tubing 49 is secured to the proximal end 50 of the second side arm 48. Upon assembly, the other end 51 of tubing segment 49 is connected to the proximal end of the suction lumen of a double lumen irrigating tube; described below. As described below in greater detail, bowel effluent that drains into the suction lumen of the double lumen irrigating tube can then drain into the drain tube through tubing segment 49 and second side arm 48 and from there through the outflow tubing 21 into the collection containers 16. By the same route, in reverse direction, suction is transmitted to the entire bowel through which the irrigating tube passes.

A second modification of the second embodiment, i.e., the double side arm embodiment, of the drain tube comprises a distal body portion which is extruded rather than molded in a fashion identical to the extruded body 41 of the embodiment of the single side arm drain tube illustrated in FIG. 5. Referring to FIG. 9, the proximal portion 53 of the drain tube is molded from a flexible or rigid polymer and includes a first side arm 31d and a reduced diameter second side arm 48d extending from first side arm 31d. If molded from a rigid polymer, the proximal end 52 of the proximal portion 53 may be molded to receive an irrigating tube tapered cuff member without the need for a separate bushing 27. The extruded distal body portion and molded proximal portion 53 can be joined in the same manner as the corresponding portions of the single side arm drain tube as shown in FIG. 5.

Figure 10:
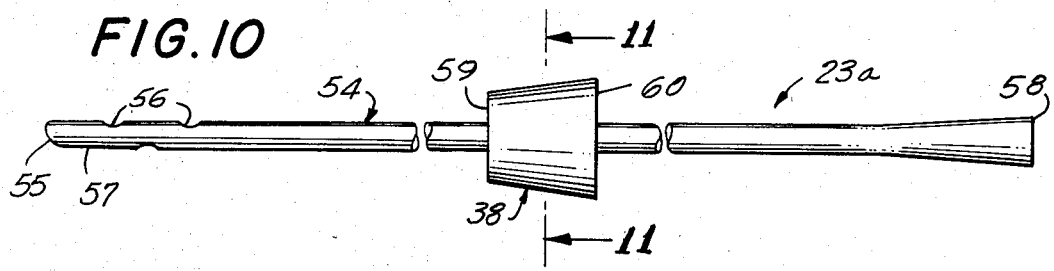
FIG. 10 is a perspective view of a first embodiment of an irrigating tube according to the invention, namely, a single lumen irrigating tube.
Figure 11:
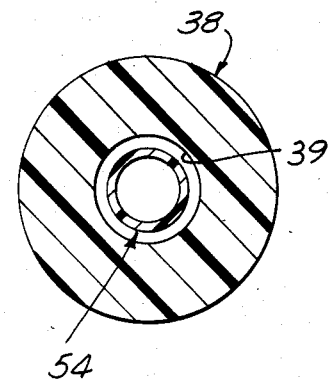
FIG. 11 is a transverse cross-sectional view taken along line 11—11 of FIG. 10.

Referring now to FIGS. 10 and 11, a first embodiment of an irrigating tube, designated 23a, includes an elongated single lumen tubular member 54 having a length sufficient so that when its distal tip portion 57 is situated in a favorable position in the cecum (or even into the distal small bowel), its proximal end 58 will extend through and beyond the inserted drain tube as described below. A tapered cuff member 38 has a central bore 39 whose diameter is slightly larger than the outer diameter of the tubular member 54 so that the tubular member freely slides within the bore 39. As noted above, when the cuff member 38 is inserted into the drain tube bushing 27, or in the case where the drain tube is formed of a rigid plastic material, into the proximal end of the primary tubular section 29, the wall of bore 39 is urged into sealing engagement with the side wall of the tubular member 54. The elongate single lumen tubular member 54 is smooth surfaced and is formed of a flexible elastomer. The distal end 55 of the tubular member 54 is open and/or one or more side apertures 56 are formed through the tubular member 54 into the single lumen exclusively in the region proximate to its distal tip portion 57. The number, precise location, and size of the apertures 56 are not critical to the function of the irrigating tube 23a. The advantage of having multiple apertures near the distal tip portion 57 is to permit more efficient suction of luminal contents when suction is applied to the proximal end 58 of the tube as it is slowly withdrawn from the bowel after irrigation has been completed as described below.

The outer diameter of the distal end 59 of the tapered cuff member 38 is slightly smaller than the inner diameter of the drain tube bushing 27 which itself is slightly smaller than the outer diameter of the proximal end 60 of the tapered cuff member. After the irrigating tube is positioned for irrigation within the bowel, passing through the drain tube (see FIG. 21), the tapered cuff member 38 is slid forwardly over the irrigating tube and plugged into the rigid bushing 27 of the drain tube 22. The inner surface of the bore 39 of the compliant tapered cuff member 38 is thus compressed around the outer surface of the tubular member 54 of the irrigating tube 22 forming a seal to prevent leakage of bowel effluent during irrigation. The proximal end 58 of the irrigating tube may be flared outwardly as shown in FIG. 10 in order to receive a tubing connector whose inner diameter is larger than the smallest inner diameter of the irrigating tube. Alternatively, the tube member 54 may be formed with a cylindrical proximal end which may be provided with a cuff of the same or similar elastomer (not shown). In any event, the proximal end 58 of irrigating tube 23a is connected to the inflow tubing 18.

Figure 12:
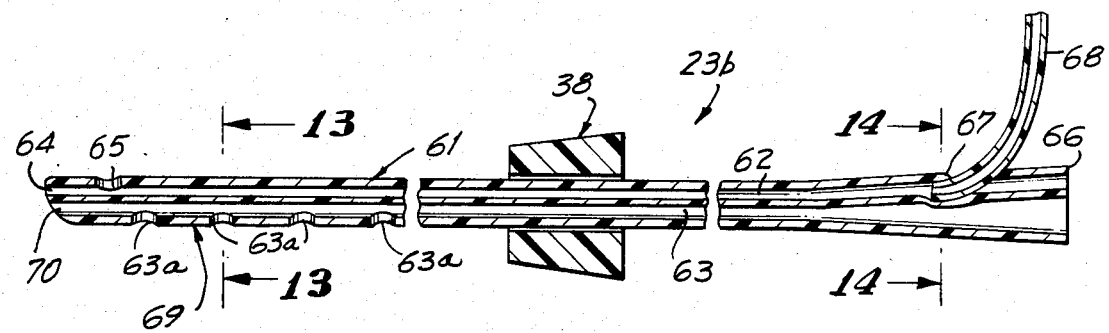
FIG. 12 is a longitudinal section view of a second embodiment of an irrigating tube in accordance with the invention, namely, a double lumen irrigating tube having apertures formed in the irrigating lumen only in and near its distal end.
Figure 13:
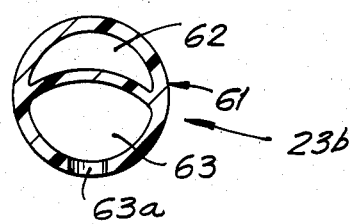
FIG. 13 is a section view taken along line 13—13 of FIG. 12.
Figure 14:
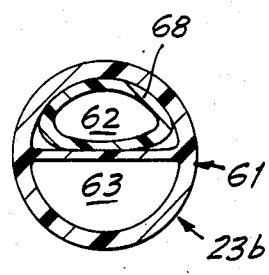
FIG. 14 is a section view taken along line 14—14 of FIG. 12.

Referring now to FIGS. 12–14, a second embodiment of an irrigating tube, designated 23b, is illustrated. The irrigating tube 23b comprises a tapered cuff member 38, identical to that described above in connection with the single lumen irrigating tube 23a, and an elongated double lumen tubular member 61 having a smooth surface and formed from a flexible elastomer similar to the single lumen tubular member 54. One of the lumens 62 functions as an irrigating lumen to deliver irrigant into the bowel. The other lumen 63 constitutes a suction lumen and facilitates evacuation of fluid and colonic waste from the bowel. The irrigating lumen 62 is open at its distal end 64 and one or more side apertures 65 are formed in the region of its distal end portion. A side aperture 67 is formed in the proximal portion of the irrigating lumen 62 through which an extension tube 68 is fixed. Extension tube 68 flares into a larger diameter as shown for attachment to the inflow tubing 18.

Figure 15:
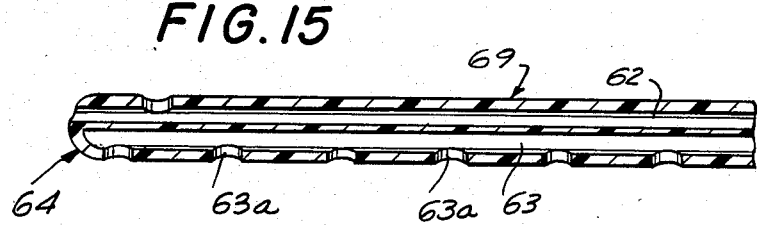
FIG. 15 is a longitudinal section view of a modification of the distal end portion of the second embodiment of the irrigating tube illustrated in FIG. 12.

The evacuation or suction lumen 63 has one or more apertures 63a formed therein over a relatively long segment of the distal portion 69 of irrigating tube 23b and opens at its distal end at an aperture 70. Alternatively, the end of the distal end portion 69 of the irrigating tube may be rounded and the suction lumen 63 closed as seen in FIG. 15 in order to facilitate passage of the irrigating tube through the bowel and to decrease the possibility of inadvertent puncturing of the bowel wall. Thus, the construction of the end of portion 69 of the irrigating tube illustrated in FIG. 15 represents a first modification of the second embodiment of the irrigating tube 23b.

Figure 16:
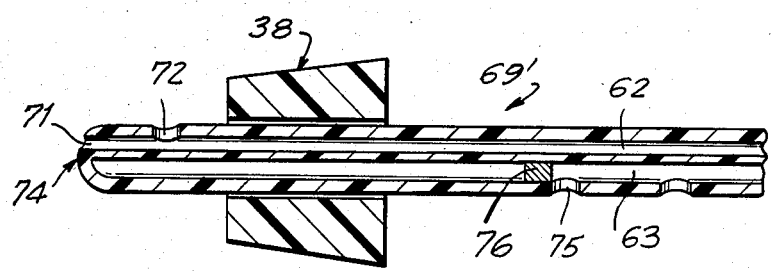
FIG. 16 is a longitudinal section view of a second modification of the distal end portion of the second embodiment of the irrigating tube illustrated in FIG. 12 and showing the tapered cuff member.

Referring to FIG. 16, a second modification of the distal portion, designated 69', of the irrigating tube 23b is illustrated which is especially suited for use in administering an intraoperative enema wherein only the tip region of the irrigating tube is inserted into the rectal tube. An aperture 71 is provided in the distal end 74 of the irrigating lumen 62 and a single side aperture 72 may be provided adjacent thereto as shown. The distal end 74 of the irrigating tube is rounded and the first aperture 75 in suction lumen 63 is formed only several centimeters from the distal end 74. A plug 76 is positioned in suction lumen 63 just distal of the most distal aperture 75 and is sealed in place. The purpose of plug 76 is to prevent contamination of the portion of the suction lumen which is distal to the first aperture 75 which would be slow to empty and thus serve to bleed contamination into the bowel even after the bowel has been cleansed. The tapered cuff 38 is slid over the irrigating tube to a position intermediate of the side aperture 72 formed in irrigation lumen 62 and the first aperture 75 formed in suction lumen 63.

The construction of the distal portion of the irrigating tube illustrated in FIG. 16 will avoid spilling of fluid onto the operating table when only the tip of the irrigating tube is inserted in the course of administering an intraoperative enema since the first and most distal suction aperture 75 remains proximal to the tapered cuff 38 outside of the drain tube. The proximal end of the suction lumen is connected to tubing 49 (FIG. 7) attached to the second smaller diameter side arm 48 of a double side arm drain tube. After the enema is administered the irrigating tube can then be advanced through the colon for unidirectional antegrade irrigation.

Figure 17:
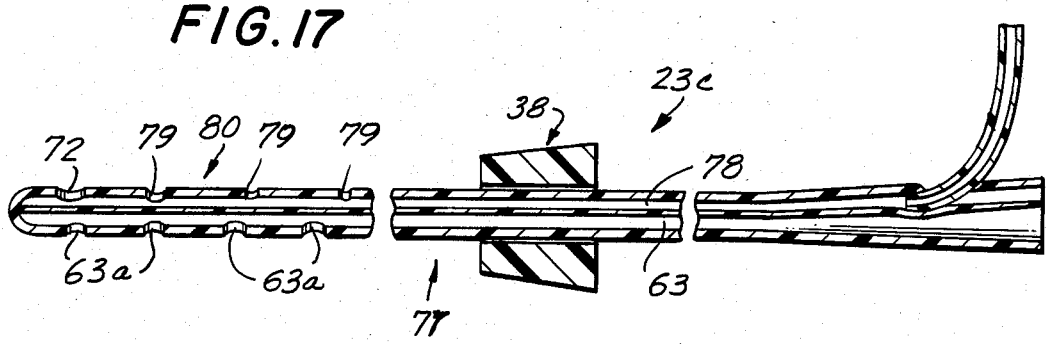
FIG. 17 is a longitudinal section view of a third embodiment of an irrigating tube in accordance with the invention, namely, a double lumen irrigating tube having apertures formed in the irrigating lumen along a relatively long segment of the distal portion thereof.

A third embodiment of an irrigating tube, designated 23c, is illustrated in FIG. 17. This embodiment is useful where an obstruction exists in the portion of the tract being irrigated as described below. Irrigating tube 23c comprises tapered cuff member 38 and a double lumen tubular member 77. The irrigating tube 23c differs from the previously described double lumen irrigating tube 23b in that the irrigating lumen 78 has in addition to a first aperture 72 located in the region of the distal tip portion, a plurality of second side apertures 79 formed over a relatively long segment of the distal portion 80 of the tube. Side apertures 79 may be arranged so that the distance between them increases in the proximal direction of the tube and/or so that the apertures become smaller in the same direction. Since the irrigating lumen 78 offers resistance to flow of fluid within it, there is a pressure drop from the proximal end of the irrigating lumen to the distal end. Spacing the apertures or varying the aperture diameters in the manner described above ensures that a relatively uniform spray is discharged from the irrigating lumen along its length.

It will be understood that all of the irrigating tubes 23 described above are intended to be available in a variety of diameters and lengths so they may be used in patients of all ages and sizes. The irrigating tubes may have circumferential ribs 80a (FIG. 21) formed along their distal portions to give the surgeon's fingers better purchase on the tube through the bowel wall which will enable him to advance the tube more expeditiously.

Figure 18:
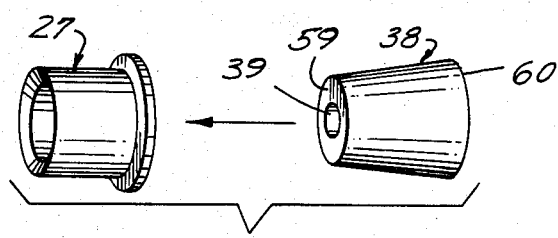
FIG. 18 is a perspective view of first embodiments of a drain tube bushing and tapered cuff member of the irrigating tube.
Figure 19:
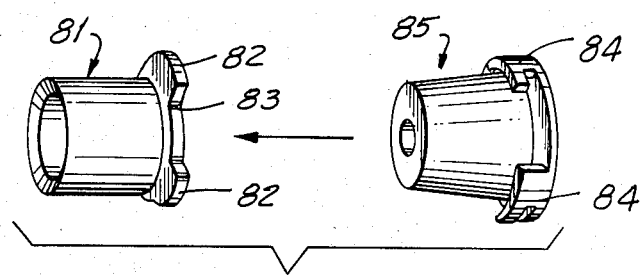
FIG. 19 is a perspective view of second embodiments of a drain tube bushing and tapered cuff member of the irrigating tube.
Figure 20:
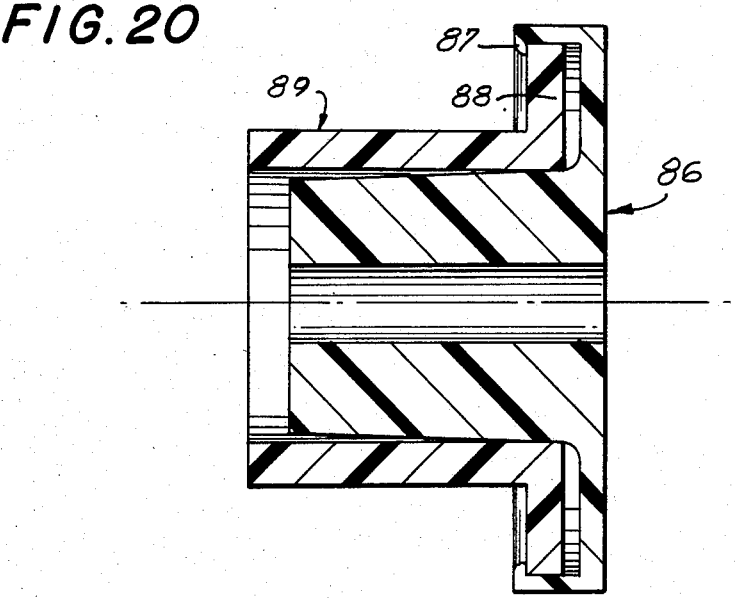
FIG. 20 is a perspective view of third embodiments of a drain tube bushing and tapered cuff member of the irrigating tube.

Three embodiments of rigid bushings 27, 81 and 89 and corresponding tapered cuff members 38, 85 and 86 are illustrated in FIGS. 18, 19 and 20, respectively. Referring to FIG. 18, the rigid bushing 27 and tapered cuff member 38 are similar to those described above in connection with the previously described embodiments of the drain and irrigating tubes. First alternative embodiments are illustrated in FIG. 19 wherein the bushing 81 and tapered cuff member 85 are provided with bayonette locking means to provide a positive locking between them. In particular, the bushing 81 has two or more curvilinear protrusions 82 extending from its outer rim 83. Corresponding stubs 84 extending inwardly from the tapered cuff member 85 are adapted to engage the protrusions 82 when the cuff member is inserted into the bushing and twisted therein. In this manner, the tapered cuff member is secured in position within the bushing and accidental dislodgement and consequent leakage during irrigation is prevented. Referring to FIG. 20, the same effects are achieved by molding the tapered cuff member 86 with an overhanging edge 87 which engages the forward surface of a flange 88 of bushing 89. It will be understood that the particular mechanism by which the tapered cuff member is secured to the bushing or to the proximal end of the primary tubular section of the drain tube in the case where the latter is formed of a rigid material such as shown in FIG. 5 is not critical to the invention and any suitable mechanism which will provide the necessary securement of the tapered cuff to the bushing and compression of the bushing bore to sealingly engage the irrigating tube can be used.

Methods in accordance with the invention utilizing the apparatus described above for the intraoperative irrigation of the gastrointestinal tract will now be described in conjunction with FIGS. 1 and 21-29.

After surgical anesthesia has been induced and with the patient in a low lithotomy position on the operating table, the distal portion of either the single or double side arm drain tube is inserted into the point of access to the portion of the gastrointestinal tract being cleansed with the aid of an obturator which is then removed. In this connection, a single side arm drain tube, such as shown in FIGS. 2-5, is used in conjunction with a single lumen irrigating tube, such as shown in FIGS. 10 and 11, while a double side arm drain tube, such as shown in FIGS. 6-9, is used in conjunction with a double lumen irrigating tube, such as shown in FIGS. 12-17. The factors which determine whether a single or double lumen irrigating tube is used are discussed below.

Figure 21:
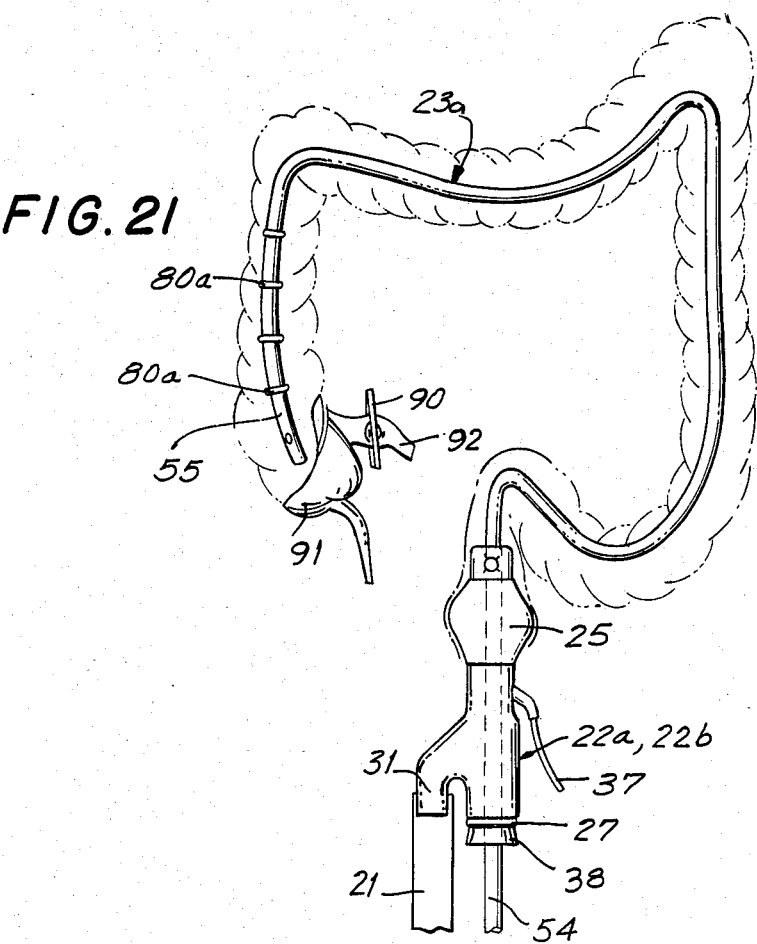
FIG. 21 is a schematic view of a patient's colon and rectum and illustrating a single side arm drain or rectal tube with a single lumen irrigating tube inserted into position in accordance with one embodiment of the method of the invention.
Figure 22:
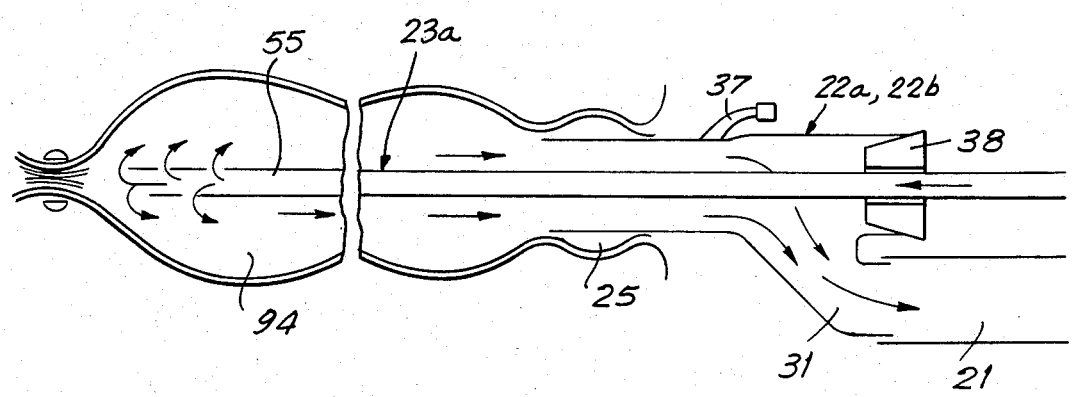
FIG. 22 is a diagramatic illustration depicting the path of irrigant as it flows through a single lumen irrigating tube, bowel, and single side arm drain or rectal tube in accordance with the invention.
Figure 23:
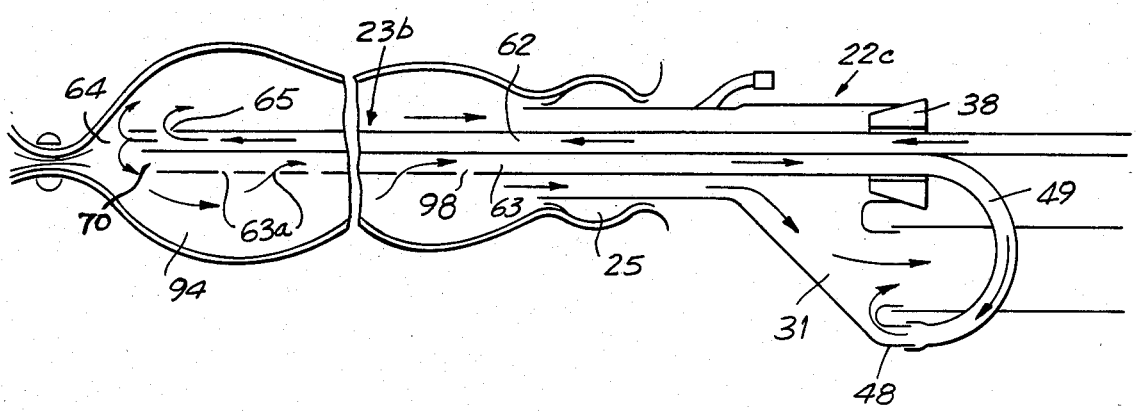
FIG. 23 is a diagramatic illustration depicting the path of irrigant as it flows through a double lumen irrigating tube in accordance with the second embodiment thereof, bowel and double side arm drain or rectal tube.

Referring to FIGS. 1, 21 and 22, an embodiment of a method of the invention wherein a single side arm drain tube 22a, 22b is used in conjunction with a single lumen irrigating tube 23a is shown and wherein the point of access to the tract portion comprises the anus so that the unidirectional irrigation of the gastrointestinal tract portion will be exclusively in the antegrade direction, i.e., towards the anus. The drain or rectal tube 22a,22b is inserted into the anus so that its distal end communicates with the tract portion being irrigated. The expandable retention cuff 25 is inflated through tubing segment 37 (FIG. 21) and adjusted so that it abuts the anal sphincter muscles to obturate the anal canal. The rectal tube can then be further secured in position with tape or by any other effective means. One end of the flexible outflow hose 21 is then connected to the side arm 31 of the rectal tube 22a, 22b while its other end is connected to the valve 21a which communicates with the collection containers 16 (FIG. 1) which may themselves be connected in series and through a suction regulator to a vacuum source.

After laporotomy is performed, an assistant inserts an appropriate one of the irrigating tubes through the primary tubular section of the rectal tube and into the bowel. As noted above, a single lumen irrigating tube 23a is used with the single side arm rectal tube 22a, 22b. The irrigating tube 23a is advanced through the bowel to its desired position through manipulation of the irrigating tube through the bowel wall by the surgeon. The irrigating tube 23a is advanced until its distal end 55 is located in the region of the closed distant end of the gastrointestinal tract portion being irrigated. Thus, if only a portion of the tract is being irrigated, the tract is occluded at the distant point of the tract portion and the irrigating tube is passed into the tract until its distal end is situated substantially at the occluded or closed distant end of the tract portion. In the situation illustrated in FIG. 21, the irrigating tube 23a is advanced until its distal end is located in the region of the cecum 91. In this connection, the irrigating tubes used in accordance with the invention are sufficiently long to allow their distal tips to be positioned at the region of the cecum and are preferably sufficiently long to allow further insertion into the distal small bowel 92 (FIG. 21) should the surgeon wish to cleanse that region of the intestine as well.

Once the irrigating tube is in position as described above, the tapered cuff member 38 is slid over the tubular member 54 of irrigating tube 23a and plugged into the bushing 27 of the rectal tube assuring a water tight seal around the irrigating tube. The inflow tubing conduit 18 connected to the irrigation reservoir spigot 5 and passing through the head of pump 10 is connected to the irrigating lumen (the only lumen in this case) of the irrigating tube 23a. It is noted that if a double lumen irrigating tube is used, as described below, the suction lumen thereof is connected to the second side arm of a double side arm drain or rectal tube. The surgeon then places a non-crushing intestinal occluding clamp 90 across the bowel just above the tip of the irrigating tube to prevent retrograde filling of the upper bowel during irrigation and antegrade contamination of the operative area during the surgical procedure performed on the irrigated bowel.

The pump 10 is then turned on and the potentiometer on the pump is set to a maximum speed which is commensurate with the size and condition of the bowel to be irrigated. The temperature of the primary and secondary irrigants are monitored and if not at the desired temperature the immersion heater is placed into the reservoir and the irrigant is heated to the appropriate temperature, e.g., body temperature.

The spigot of the reservoir 1 containing the primary irrigant is opened and the suction regulator 17 is set for the degree of suction desired whereupon air is evacuated from the bowel which collapses. The surgeon then initiates and controls the speed of irrigation by depressing the pedal of the foot-controlled potentiometer 15. The pump speed is regulated by the surgeon who is holding the bowel according to the degree of dilitation thereof.

When the effluent appears clear, the surgeon may fill the bowel with antiseptic contained in the secondary irrigant merely by opening the spigot 5 associated with the secondary irrigant reservoir 2 and closing the spigot associated with the primary irrigant reservoir 1. A higher degree of antisepsis can thereby be achieved than can be achieved by mechanical cleansing alone.

After irrigation, the irrigating tube 23a can be detached from the conduit 18 from the pump and connected to suction whereupon the bowel can be suctioned empty as the colonic tube is withdrawn.

The choice of which irrigating tube and which corresponding drain tube is used to irrigate a particular patient depends largely on the anatomy and pathology of the patient. For small children the single lumen irrigating tube with the single side arm drain tube may be most appropriate due to the small caliber and relatively short length of a child's bowel. Moreover, in the case where an adult has a colonic obstruction which is complete and which will not allow passage of a tube beyond it, the single lumen irrigating tube is again most appropriate to cleanse the short segment distal to the obstructing lesion.

Referring to FIG. 22 wherein the path of the irrigant through the bowel is illustrated utilizing a single lumen irrigating tube 23a and a single side arm rectal tube 22a, 22b, the irrigant travels through the irrigating tube 23a and is discharged therefrom at its distal end 55 to enter the bowel lumen 94 where it washes the contents unidirectionally in an antegrade direction towards the rectal tube 22a, 22b. Thus, the irrigant carries the bowel contents as effluent into the rectal tube where it is discharged through the side arm 31 into the outflow tubing 21 into collection containers 16.

In the case where the patient is an adult having a nonobstructed colon, a double lumen irrigating tube, such as that designated 23b in FIGS. 12-15, in conjunction with a double side arm drain tube, such as that designated 22c in FIGS. 6-9, is indicated. The path of irrigant flow through the instruments and the bowel in this case is diagramatically illustrated in FIG. 23. Primary irrigant is pumped through tubing 18 into the irrigating lumen 62 and is discharged into the bowel at or near the distal end 64 of the irrigating lumen 62 through an aperture formed at the distal tip and/or through one or more side apertures 65 formed in the distal end portion of the irrigated lumen. The irrigant enters the bowel lumen where it washes the colon content exclusively in an antegrade direction (in the case where the point of access to the tract is the anus). The outflow tubing 21 transmits suction into both the suction lumen 63 of the irrigating tube 23b (through tubing segment 49 and second side arm 48) as well as into the bowel lumen through the primary tubular section of the rectal tube. The irrigant carrying the colonic material is both suctioned into the suction lumen 63 through side apertures 63a as well as directly into the rectal tube 22c. The effluent is suctioned from the suction lumen 63 through tubing 49 and second side arm 48 and through the primary tubular section of the rectal tube through the first side arm 31 into the outflow tubing 21 to the collection containers 16. When irrigation has been completed, the entire bowel portion that has been irrigated is suctioned empty simultaneously and rapidly through the multiple side apertures 63a of suction lumen 63. The suction may then be turned off and the irrigating tube removed.

Figure 24:
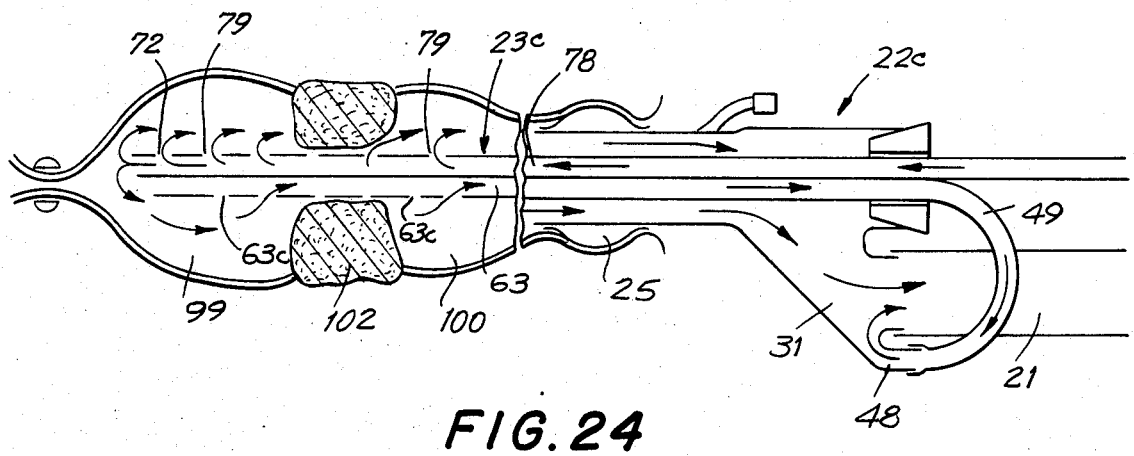
FIG. 24 is a diagramatic illustration depicting the path of irrigant as it flows through a double lumen irrigating tube in accordance with the third embodiment thereof, stenotic bowel, and double side arm drain or rectal tube.

Referring to FIG. 24, another embodiment of a method according to the invention is shown wherein the anus comprises the point of access to the tract portion being irrigated. However, unlike the situation shown in FIGS. 21-23, a significant luminal obstruction, such as an obstruction 102, exists which presents enough patency to permit the passage of a tube. In this case the portion 100 of the bowel which is below the obstruction 102 may not be adequately cleansed using the type of irrigating tube 22b described above. This is because the obstruction 102 limits the rate that irrigant can be infused into the portion 99 of the bowel above the obstruction. Thus, the bowel portion 99 above the obstruction can distend with fluid while the bowel portion 100 below the obstruction 102 remains collapsed because of easy outflow from this portion. Since the more distal bowel portion below the obstruction never distends well, cleaning of this segment may be difficult.

Accordingly, this condition indicates the use of the third type of irrigating tube, designated 22c, shown in FIG. 17. The irrigating tube 22c functions well since it permits a more uniform irrigation of all segments of the bowel. Referring to FIG. 24, irrigant flowing through the irrigating lumen 78 is discharged through the first distal aperture 72 and the plurality of side apertures 79 formed along the ma3or length of the distal portion of the irrigating lumen and enters the bowel lumen simultaneously at many points along its length. The bowel is washed and the irrigant is suctioned into the suction lumen 63 through the side apertures 63c or into the rectal tube 22c directly below the obstruction 102. In this manner the bowel can be uniformly distended with irrigant both above and below the partial obstruction 102.

Since it may be necessary to pass the third type of irrigating tube 23c through partially obstructed areas, such irrigating tubes may advantageously be formed with a smaller diameter and with stiffer and thinner walls to provide more luminal area for a given outer diameter. For this reason, such irrigating tubes may be constructed from an elastomer with a higher durometer value.

If the operation to be performed involves the rectum, it may be necessary to take further steps to clean the rectum because feces can accumulate around the drain or rectal tube tip and cuff during a regular irrigation. A second intestinal occluding clamp is then placed around the intraperitoneal portion of the rectum after the irrigating tube has been withdrawn. If the single lumen irrigating tube had been used during the irrigation it is positioned so that its tip is just distal to the occluding clamp.

If a double lumen irrigating tube had been used for irrigation, then when irrigation is completed a single lumen irrigating tube or a short conventional rectal tube may be connected to the tubing 18 from pump 10 and inserted through the drain tube to the level of the occluding clamp. The retention cuff 25 is then deflated and the drain tube removed. The rectum is then thoroughly irrigated and the effluent is allowed to pass out the anus around the irrigating tube. It is therefore advisable to have a means, such as an enema ring device with a drain, in order to retain and collect the effluent that may otherwise spill during this secondary procedure.

The tube can then be removed and the operation can proceed with a thoroughly clean colon and rectum.

Figure 25:
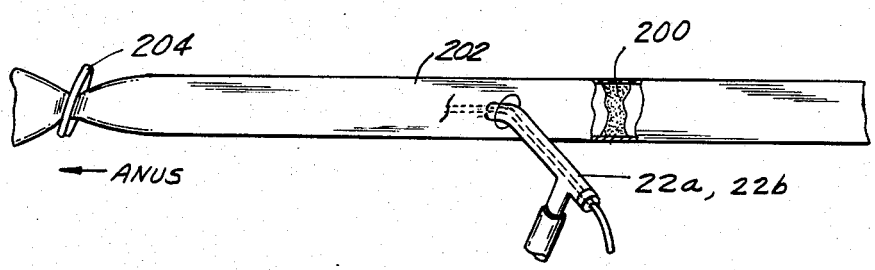
FIG. 25 is a schematic view of a patient's colon and illustrating a single side arm drain tube with a single lumen irrigating tube inserted into position in accordance with another embodiment of the method of the invention.

Referring to FIG. 25, an embodiment of a method of the invention wherein a single side arm drain tube 22a, 22b is used in conjunction with a single lumen irrigating tube 23a is shown and wherein the point of access to the tract portion comprises a colotomy or enterotomy. This embodiment may be advantageously used where a complete obstruction 200, such as a tumor, exists in the tract and it is desired to cleanse the portion of the tract below obstruction 200, i.e., wherein the tract portion is on the side of obstruction 200 closer to the anus. It will be understood, however, that in the case where it is desired to cleanse only a lower portion of an unobstructed tract, a clamp may occlude the tract at the position of obstruction 200. The point of access to the tract portion in which the drain tube 22a, 22b is positioned comprises a colotomy or enterotomy 202 below and adjacent to the obstruction 200. The irrigating tube 23a is passed through the drain tube 22a, 22b and into the tract portion until its distal end portion is situated adjacent the distant tract point formed by clamp 204. Irrigation proceeds unidirectionally in the same manner as described above in connection with the embodiment shown in FIGS. 21 and 22. However, the unidirectional irrigation proceeds in the retrograde direction, i.e., towards the mouth, rather than in the antegrade direction as in the previously described embodiments.

Referring to FIGS. 26-29, an embodiment of a method of the invention wherein a modified double side arm drain tube 220, similar to drain tube 22c, is used in conjunction with a double lumen irrigating tube 23b is shown wherein a high grade or complete obstruction exists in the bowel and wherein the tract portion is cleansed through an end of a transected bowel rather than through a colotomy. According to this method, the bowel segment containing obstructing tumor 201 (FIG. 26a) is resected between clamps or by the use of intestinal staples 210 (FIGS. 26a and 26b). After transection of the bowel, the tumor 201 is excised (FIG. 26b) and the proximal cut end of the transected bowel is then placed through a sterile drape 212 which contains a hole of a diameter similar to the diameter of the bowel (FIG. 25c). The hole has a cuff or collar to which the outer layer of the bowel wall or serosa is sewn at a point about two to ten centimeters from the transected edge of the bowel. In this manner a seal is formed between the bowel and drape 212 so that no contaminated material can pass to the other side of the drape. A first surgeon then opens the transected bowel edge (FIG. 26d) and with the aid of the obturator passes the drain tube into the open end of the bowel (FIG. 26e). The field on the first surgeon's side of the drape 212 is now contaminated while a second surgeon on the opposite side of the drape, and the field beneath the drape remain sterile.

The double side arm drain tube 220 has a modified distal end. In place of the expandable cuff (FIG. 27) or proximal to the cuff 25 (FIG. 28), a fabric cuff 222 is provided to which the free edge of the bowel is sewn (FIG. 26e) to form a water tight seal. In another modification (FIG. 29), the drain tube can be molded with a circumferential groove or channel 224 either near the distal tip of the drain tube in place of (or in addition to) the expandable cuff for receiving a tube clamp 226 placed around the bowel end over the drain tube. The clamp and groove may also be used in conjunction with the cloth cuff 222.

Figure 26A:
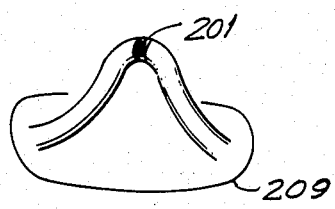
FIGS. 26(a)–26(i) are schematic illustrations showing a sequence of steps wherein the method and apparatus of the invention are utilized in cleansing a transected bowel lumen portion proximal to a high grade or complete obstruction.
Figure 26B:
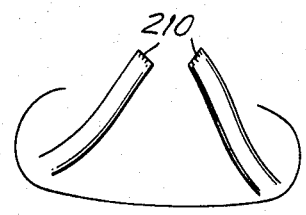
Figure 26C:
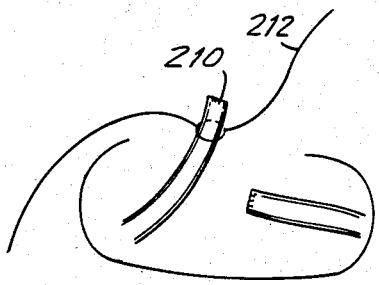
Figure 26D:
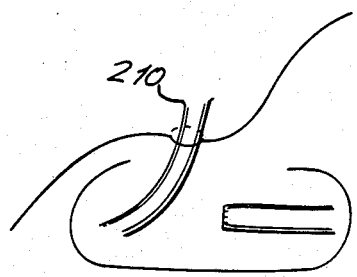
Figure 26E:
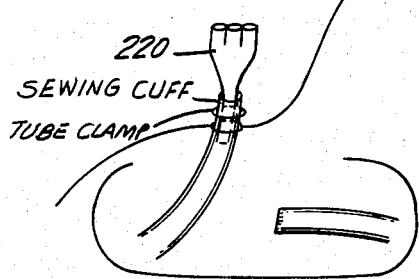
Figure 26F:
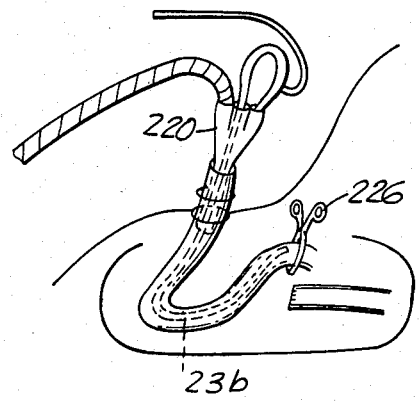
Figure 26G:
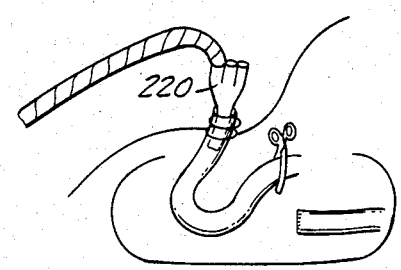
Figure 26H:
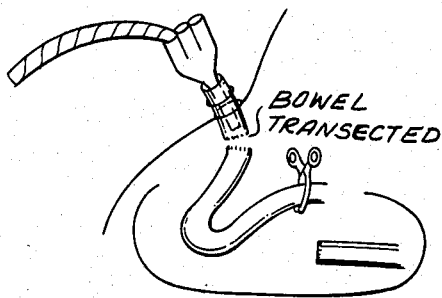
Figure 26I:
Figure 27:
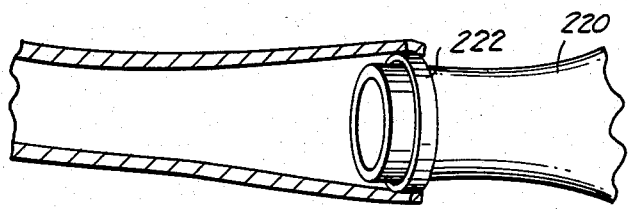
FIGS. 27–29 are schematic perspective view illustrating modifications of drain tubes used in connection with cleansing a transected bowel lumen.
Figure 28:
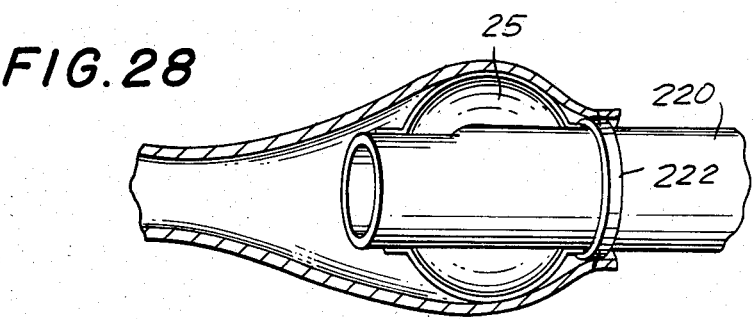
Figure 29:
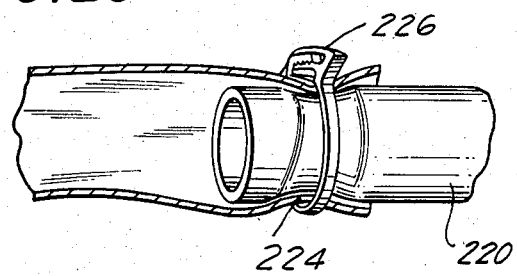

Once the drain tube 220 is sealed to the bowel edge by any of the aforementioned techniques, the first surgeon inserts the irrigating tube 23b (FIG. 26f) through the drain tube 220 and with the aid of the second surgeon manipulates the irrigating tube through the bowel wall until its distal end portion reaches the distant point, defined by clamp 226, of the bowel tract portion to be cleansed. The irrigating tube cuff is then sealed within the drain tube and the bowel is irrigated as described above. The irrigating tube 23b is removed, the bowel is transected below the drape 212 (FIG. 26g) and the drape, along with the attached short bowel segment, are removed (FIGS. 26h and 26g). The contaminated surgeon changes gown and gloves and resumes his role in the surgery. The bowel portion distal to the obstruction can then be cleansed in a similar manner or by introducing the drain and irrigating tubes through the anus as previously described, or by infusing irrigant distal to the obstruction and draining the irrigant by a large diameter drain tube.

Figure 30:
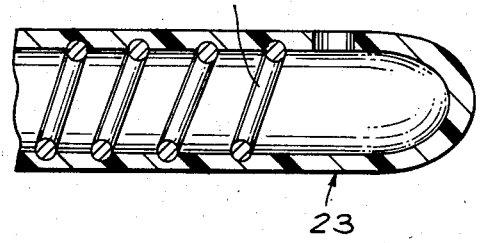
FIGS. 30 and 31 are views illustrating additional modifications of irrigating tubes which facilitate insertion through the bowel lumen.

In passing the irrigating tube through the colon to the cecum, the tube must advance through the spenic flexure which is the point where the bowel takes its sharpest turn. In order to facilitate the manipulation of the irrigating tube to achieve a swift advancement to the cecum, a coiled spring 230 may be molded into the irrigating tube as illustrated in FIG. 30 to provide both axial stiffness as well as lateral flexibility. This construction will also prevent kinking or collapse of the irrigating tube. Moreover, by providing a greater distance between the coils of the spring at the distal end portion of the irrigating tube, the distal end portion may be given greater flexibility than the remainder of the tube.

Figure 31:
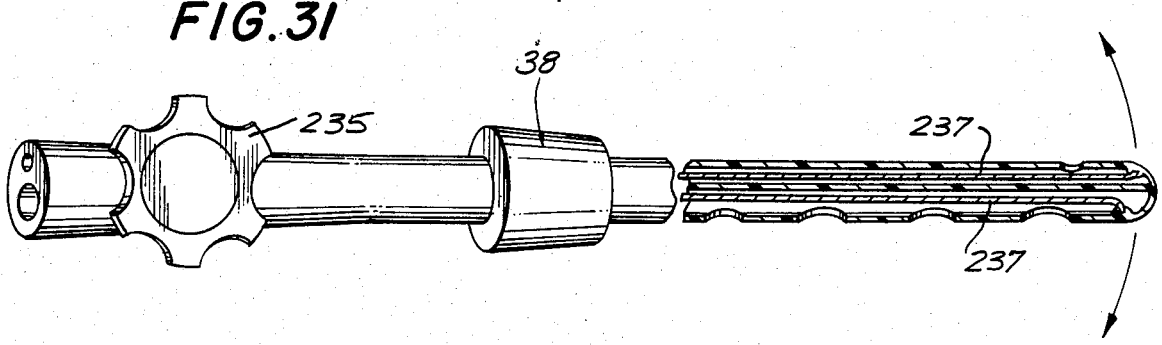

The irrigating tube may be provided with means for steering its distal end portion in a manner similar to conventional endoscopes. Referring to FIG. 31, a control unit including a rotatable knob 235 and control cables 237 may be provided which will guide the distal end of the tube 23 by suitable rotation of knob 235.

Other possibilities for facilitating the passage of the irrigating tube through the colon include the addition of a stylet or guide wire into the proximal end of the suction lumen of a double lumen irrigating tube to its distal tip. The stylet or guide wire, which is removed after successful passage of the irrigating tube to the cecum and prior to irrigation, will also serve to stiffen the tube. Another possibility is the addition of a narrow third lumen to serve as an inflation-deflation lumen for a single balloon located at the distal end of the tube, or for two balloons located at the distal end separated by a small distance, e.g., several inches. When inflated while the tube is within the bowel, the balloon or balloons enable the surgeon to obtain a good grip on the tube so that it can be more easily manipulated through the bowel.

The apparatus of the invention may also be advantageously used in order to control body temperature by adjusting the temperature of the irrigant in the reservoir 1 to a desired temperature and circulating the irrigant through the bowel as described above. Since the bowel presents a large surface area and a large blood supply, a good heat transfer will result between the irrigant and the body.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. Apparatus for undirectional irrigation of at least a portion of the gastrointestinal tract including the bowel, said gatrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof;

irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communications at its proximal end with a source of irrigant, said irrigating tube means having first aperture means formed therein communicating with said at least one lumen and opening externally of said irrigating tube means only at a region thereof situated substantially proximate to said distal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means; and fluid sealing means extending between said primary tubular section of said drain tube means and said tubular member portion of said irrigating tube for preventing effluent entering into said distal end portion of said primary tubular section from being discharge from said proximal end portion thereof, said fluid sealing means including a cuff member having a bore formed therethrough through which at least a portion of said tubular member of said irrigating tube passes, said cuff member adapted to sealingly engage said primary tubular section of said drain tube means;

whereby with said drain tube means and irrigating tube means inserted in the gastrointestinal tract portion, irrigant conducted into the proximal end of said at least one lumen flows therethrough and is discahrged therefrom through said first aperture means at said region situated substantially proximate to said distal end of said irrigating tube means at the occlued distant point of the gastrointestinal tract portion whereupon said irrigant flows unidirectionally through said gastointestinal tract portion towards said drain tube means whereupon irrigant carrying the contents or said gastointestinal tract portion in the form of effluent enters into said drain tube means and is discharged therefrom through said effluent conducting means thereof.

2. Apparatus for unidirectional irrigation of at least a portion of the gastointestinal tract including the bowel, said gastrointestinal tract portion to be irrigated defined between a point of access and an occluded distant point, comprising:

drain the means for collecting effluent from the gastointestinal tract portion, said drain tube means including a primary tubular section having a distal end portion and a proximal end portion and further including means for conducting effluent from the gastrointestinal tract portion being irrigated to a region external thereof;

irrigating tube means for conducting irrigant to a region proximate to an occluded distant point in the gastrointestinal tract portion, said irrigating tube means having a distal end and a proximal end and including an elongated tubular member having at least one lument extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means;

said drain tube means and said irrigating tube means being formed so that a portion of said elongate tubular merber of said irrigating tube means is situated within said primary tubular section of said drain tube means, said elongated tubular member of said irrigating tube means having a length such that upon said insertion of said irrigating tube means in the gastrointestinal tract portion, said distal end of said irrigating tube means is situated substantially at the occluded distant point of the gastrointestinal tract portion and said proximal end of said irrigating tube means is situated externally of said proximal end portion of said drain tube means; and sealing means extending between said primary tubular section of said drain tube means and said tubular member portion of said irrigating tube for preventing effluent entering into said distal end portion of said primary tubular section from being discharged from said proximal end portion thereof, said fluid sealing means including a cuff member having a bore formed therethrough through which at least a portion of said tubular member of said irrigating tube passes, and a bushing member adapted to be fixed in said proximal end portion of said drain tube means, said cuff member adapted to sealingly engaging said bushing member;

whereby with said drain tube means and irrigating tube means inserted, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

3. The combination of claim 2 wherein said cuff member is formed of a compliant material and wherein said bore formed therethrough has a diameter which is slightly greater than the diameter of said tubular member portion which passes therethrough so that said cuff member, when disengaged from said bushing, can freely slide thereover, said cuff member having a tapered frusto-conical outer configuration having a distal end portion adapted to be received in said bushing to sealingly engage the same whereupon said cuff member bore is compressed into sealing engagement with said portion of said tubular member of said irrigating tube means.

4. The combination of claim 3 wherein said effluent conducting means for said tube means include a first side arm communicating at one end thereof with said primary tubular section, and further including a second side arm communicating with said primary tubular section.

5. The combination of claim 2 wherein said effluent conducting means of said drain tube means include a first side arm communicating at one end thereof with said primary tubular section, and further including a second side arm communicating with said primary tubular section.

6. Apparatus for unidirectional irrigation of at least a portion of the gastrointestinal to be irrigated the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof; and irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means, and wherein said elongate tubular member of said irrigating tube means has a first irrigating lumen constituting said at least one lumen and a second suction lumen extending between distal and proximal ends thereof and adapted to be connected in a region of its proximal end to a suction source, said irrigating tube means having second aperture means formed therein communicating with said suction lumen and opening externally of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means in the gastrointestinal tract portion, said distal end of said irrigating tube means is situated substantially at the occluded distant point of the gastrointestinal tract portion and said proximal end of said irrigating tube means is situated externally of said proximal end portion of said drain tube means, whereby with said drain tube means and irrigating tube means inserted, irrigant conducted into the proximal end of said at least one lumen flows therethrough and is discharged therefrom through said first aperture means at said region situated substantially proximate to said distal end of said irrigating tube means at an occluded distant point of the gastrointestinal tract portion whereupon said irrigant flows undirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

7. The combination of claim 6 wherein said second aperture means include a plurality of apertures formed in a side of said irrigating tube means along a segment of said distal end portion of said irrigating tube.

8. The combination of claim 7 wherein said effluent conducting means of said drain tube means include a first side arm communicating at one end thereof with said primary tubular section, and further including a second side arm communicating with said primary tubular section.

9. The combination of claim 6 wherein said effluent conducting means of said drain tube means include a first side arm communicating at one end thereof with said primary tubular section and having another end adapted to be connected to a source of suction; and a second tubular side arm communicating at one end thereof with and extending from said primary tubular section, and tubing means fluidly interconnecting said suction lumen of said irrigating tube and another end of said second tubular side arm.

10. A drain tube for use in the irrigation of at least a portion of the gastrointestinal tract including the bowel, said gastrointestinal tract portion to be irrigated defined between a point of access and an occluded distant point, comprising:

a primary tubular section having a distal end portion and a proximal end portion and further including means for conducting effluent from said gastrointestinal tract portion being irrigated to a region external thereof, said effluent conducting means including a first tubular side arm communicating at one end thereof with said primary tubular section and having another end fluidly connected to a source of suction, said drain tube further including a second tubular side arm communicating at one end threof with and extending from said primary tubular section.

11. A method for irrigating at least a portion of the gastrointestinal tract, comprising the steps of:

passing a distal end of an irrigating tube through a point of access to the gastrointestinal tract to a distant point in the tract beyond which irrigation is not desired, the point of access being an enterotomy in the tract, the irrigating tube having first aperture means formed therein only in the region substantially proximate to the distal tip thereof, said passing step including the steps of inserting an obturator to limit spillage upon introduction of a drain tube, introducing a relatively short drain tube having a relatively large diameter a limited distance into the point of access to the gastrointestinal tract being irrigated, and passing the irrigating tube through the drain tube;

in the case where the tract is not already occluded at the distant point, occluding the tract at the distant point; and introducing irrigant into the irrigating tube through a proximal end thereof;

whereby irrigant passes through the irrigating tube and is discharged therefrom through the aperture means into the gastrointestinal tract portion being irrigated at the region of the occluded distant point thereof and flows unidirectionally in the form of effluent and enters the short, large diameter drain from which it is discharged for collection.

12. Apparatus for unidirectional irrigation of at least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof said drain tube means further including means for retaining and positioning said drain tube means in the gastrointestinal tract portion at the point of access, said retaining and positioning means including an inflatable retention cuff situated externally of said distal end portion of said primary tubular section of said drain tube means, and tubing means communicating with said retention cuff for selectively inflating and deflating the same, said tubing means comprising an inflation-deflation lumen formed in a wall of said drain tube means so as not to extend within said primary tubular section thereof, and wherein said effluent conducting means include a first side arm communicating at one end thereof with said primary tubular section, and further including a second side arm communicating with said primary tubular section;

irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

13. Apparatus for unidirectional irrigation of at least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof, said effluent conducting means including a first side arm communicating at one end thereof with said primary tubular section, and further including a second side arm communicating with said primary tubular section; and irrigating tube means for conducting irrigant to a region proximate to an occluded distant point in the gastrointestinal tract portion, said irrigating tube means having a distal end and proximal end and including an elongate tubular member having at least one lumen extending between said distal and proximal ends and in fluid communication at its proximal end with a source of irrigant, said irrigating tube means having a single aperture formed at said distal end of said irrigating tube means communicating with said at least one lumen and opening externally of said irrigating tube means only at a region thereof situated substantially proximate to said distal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

14. Apparatus for undirectional irrigation of at least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof, said effluent conducting means of said drain tube means including a first side arm communicating at one end thereof with said primary tubular section, and further including a second side arm communicating with said primary tubular section; and irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means;

extension tube means communicating at one end with said proximal end of said at least one lumen is in fluid communication another end with a source of irrigant;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

15. Apparatus for unidirectional irrigation of at least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for collecting conducting effluent from the gastrointestinal tract portion being irrigated to a region external thereof, said effluent conducting means including a first side arm communicating at one end thereof with said primary tubular section, and further including a second side arm communicating with said primary tubular section; and irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communication at its proximal end with a source of irrigant, said irrigating tube means having at least two apertures formed in a side of said irrigating tube means at a region thereof situated substantially proximate to said distal end communicating with said at least one lumen and opening externally of said irrigating tube means only at a region thereof situated substantially proximate to said distal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigate carrying the contents of said gastrointestinal tract portion in the form of effluent enters into the drain tube means and is discharged therefrom through said effluent conducting means thereof.

16. Apparatus for undirectional irrigation of at least a portion of the gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof, said effluent conducting means including a first side arm communicating at one end thereof with said primary tubular section, and further including a second side arm communicating with said primary tubular section; and irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means, and second aperture means formed therein communicating with said at least one lumen and opening externally of said irrigating tube means along a segment of said distal portion thereof, whereby said irrigating tube is adapted for use where the portion of the gastrointestinal tract being irrigated has a partial obstruction present therein such that respective portions of said second aperture means are situated distally and proximally of said obstruction;

said drain tube means and said irrigating tube means being formed so that a portion of said elongate tubular member of said irrigating tube means is situated within said primary tubular section of said drain tube means, said elongate tubular member of said irrigating tube means having a length upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

17. Apparatus for unidirectional irrigation of at least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof said effluent conducting means including a first side arm communicating at one end thereof with said primary tubular section, and further including a second side arm communicating with said primary tubular section; and irrigating tube means for conducting irrigant to a region proximate to an occluded distant point in the gastrointestinal tract portion, said irrigating tube means having a distal end and a proximal end and including an elongate tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means and second aperture means formed therein communicating with said at least one lumen and opening externally of said irrigating tube means, said second aperture means including a plurality of mutually spaced apertures formed along a segment of said distal portion of said irrigating tube means, the size of said apertures of said second aperture means diminishing in the direction of said proximal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

18. Apparatus for unidirectional irrigation of at least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a primary tubular section having a distal end portion and a proximal end portion and further including means for conducting effluent from the gastrointestinal tract portion being irrigated to a region external thereof, said effluent conducting means including a first side arm communicating at one end thereof with said primary tubular section, and further including a second side arm communicating with said primary tubular section; and irrigating tube means for conducting irrigant to a region proximate to an occluded distant point in the gastrointestinal tract portion, said irrigating tube means having a distal end and a proximal end and including an elongated tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means and second aperture means formed therein communicating with said at least one lumen and opening externally of said irrigating tube means, said second aperture means including a plurality of mutually spaced apertures formed along a segment of said distal portion of said irrigating tube means, the distance between adjacent apertures of said second aperture means increases with direction of said proximal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

19. Apparatus for unidirectional irrigation of a least a portion of the gastrointestinal tract including the bowel, said gastrointestinal tract portion to be irrigated defined between a point of access and an occluded distant point, comprising:

drain tube means for collecting effluent from the gastrointestinal tract portion, said drain tube means including a relatively large diameter primary tubular section having a distal end portion and a proximal end portion and further including means for conducting effluent from the gastrointestinal tract portion being irrigated to a region external thereof, said effluent conducting means comprising a tubular side arm communicating with said primary tubular section, said tubular side arm having a relatively large diameter, and a second side arm communicating with said primary tubular section; and irrigating tube means for conducting irrigant to a region proximate to an occluded distant point in the gastrointestinal tract portion, said irrigating tube means having a distal end and a proximal end and including a relatively small diameter elongate tubular member having at least one lumen extending between said distal and proximal ends and in fluid communication at its proximal end with a source of irrigant, said irrigating tube means having first aperture means formed therein communicating with said at least one lumen and opening externally of said irrigating tube means only at a region thereof situated substantially proximate to said distal end of said irrigating tube means;

said drain tube means and said irrigating tube means being formed so that a portion of said elongate tubular member of said irrigating tube means is situated within said primary tubular section of said drain tube means, said elongate tubular member of said irrigating tube means having a length such that upon said insertion of said irrigating tube means, said distal end of said irrigating tube means is situated substantially at the occluded distant point of the gastrointestinal tract portion and said proximal end of said irrigating tube means is situated externally of said proximal end portion of said drain tube means;

whereby with said drain tube means and irrigating tube means inserted in the gastrointestinal tract portion, irrigant conducted into the proximal end of said at least one lumen flows therethrough and is discharged therefrom through said first aperture means at said region situated substantially proximate to said distal end of said irrigating tube means at the occluded distant point of the gastrointestinal tract portion whereupon said irrigant flows unidirectionally through said gastrointestinal tract portion towards said drain tube means whereupon irrigant carrying the contents of said gastrointestinal tract portion in the form of effluent enters into said drain tube means and is discharged therefrom through said effluent conducting means thereof.

20. A drain tube for use in the irrigation of at least a portion of the gastrointestinal tract including the bowel, said gastrointestinal tract portion to be irrigated defined between a point of access and an occluded distant point, comprising:

a primary tubular section having a distal end portion and a proximal end portion, means for conducting effluent from said gastrointestinal tract portion being irrigated to a region external thereof, said effluent conducting means including a first tubular side arm communicating at one end thereof with said primary tubular section and having another end adapted to be connected to a source of suction and a second tubular side arm communicating at one end thereof with said primary tubular section and means for retaining and positioning said drain tube in said inserted position including an inflatable retention cuff situated externally of said distal end portion of said primary tubular section and an inflation-deflation lumen formed in a wall of said drain tube means so as not to extend within said primary tubular section thereof.

21. The combination of claim 1 wherein said cuff member is formed of a compliant material and wherein said bore formed therethrough has a diameter which is slightly greater than the diameter of said tubular member portion which passes therethrough so that said cuff member, when disengaged from said drain tube means, can freely slide over said tubular member, said cuff member having a tapered frusto-conical outer configuration having a distal end portion adapted to be received in said proximal end portion of said primary tubular section of said drain tube means to sealingly engage the same whereupon said cuff member bore is compressed into sealing engagement with said portion of said tubular member of said irrigating tube means.

* * * * *